US011550075B2

(12) United States Patent
Okazaki et al.

(10) Patent No.: US 11,550,075 B2
(45) Date of Patent: Jan. 10, 2023

(54) METAL DETECTOR, HANDHELD POWER TOOL COMPRISING THIS METAL DETECTOR, METAL DETECTION METHOD, AND METAL DETECTION PROGRAM

(71) Applicant: OMRON CORPORATION, Kyoto (JP)

(72) Inventors: Ryoji Okazaki, Kyoto (JP); Kohei Fujio, Kyoto (JP)

(73) Assignee: OMRON CORPORATION, Kyoto (JP)

( * ) Notice: Subject to any disclaimer, the term of this patent is extended or adjusted under 35 U.S.C. 154(b) by 0 days.

(21) Appl. No.: 17/528,214

(22) Filed: Nov. 17, 2021

(65) Prior Publication Data

US 2022/0196873 A1 Jun. 23, 2022

(30) Foreign Application Priority Data

Dec. 17, 2020 (JP) ............................ JP2020-209574

(51) Int. Cl.

*G01V 3/08* (2006.01)
*G01V 3/10* (2006.01)
*G01V 3/165* (2006.01)
*G01N 33/38* (2006.01)
*G01R 33/00* (2006.01)
*G01V 3/15* (2006.01)
(Continued)

(52) U.S. Cl.

CPC ........... *G01V 3/165* (2013.01); *G01N 33/383* (2013.01); *G01R 33/0047* (2013.01); *G01V 3/104* (2013.01); *G01V 3/107* (2013.01); *G01V 3/15* (2013.01); *G01S 13/0209* (2013.01); *G01S 13/86* (2013.01); *G01S 13/885* (2013.01)

(58) Field of Classification Search

CPC .......... G01V 3/165; G01V 3/104; G01V 3/17; G01V 3/15; G01V 3/107; G01N 33/383; G01R 33/0047; G01S 13/885; G01S 13/0209; G01S 13/86

USPC .................. 324/67, 323, 326, 329, 330, 334

See application file for complete search history.

(56) References Cited

U.S. PATENT DOCUMENTS

2011/0181300 A1* 7/2011 Bowring ................ G01S 7/411 702/155
2017/0315226 A1* 11/2017 Bowring ................ G01S 7/024
(Continued)

FOREIGN PATENT DOCUMENTS

JP 2020-60405 A 4/2020

*Primary Examiner* — Raul J Rios Russo
(74) *Attorney, Agent, or Firm* — Metrolex IP Law Group, PLLC

(57) ABSTRACT

A metal detector 20 includes a detection signal acquisition unit 31, a threshold value setting and updating unit 32, and a determination unit 33. The detection signal acquisition unit 31 acquires a detection signal that changes according to the detection strength for a rebar W1 contained in concrete W, on the surface of the concrete W. The threshold value setting and updating unit 32 sets a threshold value in order to determine the presence or absence of the rebar W1 on the basis of the maximum value and/or the minimum value included in the acquisition results for the detection signal acquired by the detection signal acquisition unit 31. The determination unit 33 determines the presence or absence of the rebar W1 by using the threshold value set in the threshold value setting and updating unit 32.

18 Claims, 25 Drawing Sheets

(51) Int. Cl.

| | |
|---|---|
| *G01S 13/88* | (2006.01) |
| *G01S 13/02* | (2006.01) |
| *G01S 13/86* | (2006.01) |

(56) References Cited

U.S. PATENT DOCUMENTS

| | | | | |
|---|---|---|---|---|
| 2019/0285585 | A1* | 9/2019 | Itoi | G01N 33/383 |
| 2019/0285586 | A1* | 9/2019 | Itoi | G01R 33/072 |
| 2020/0110139 | A1* | 4/2020 | Chen | G01R 33/066 |
| 2022/0193846 | A1* | 6/2022 | Okazaki | B23B 45/00 |

* cited by examiner

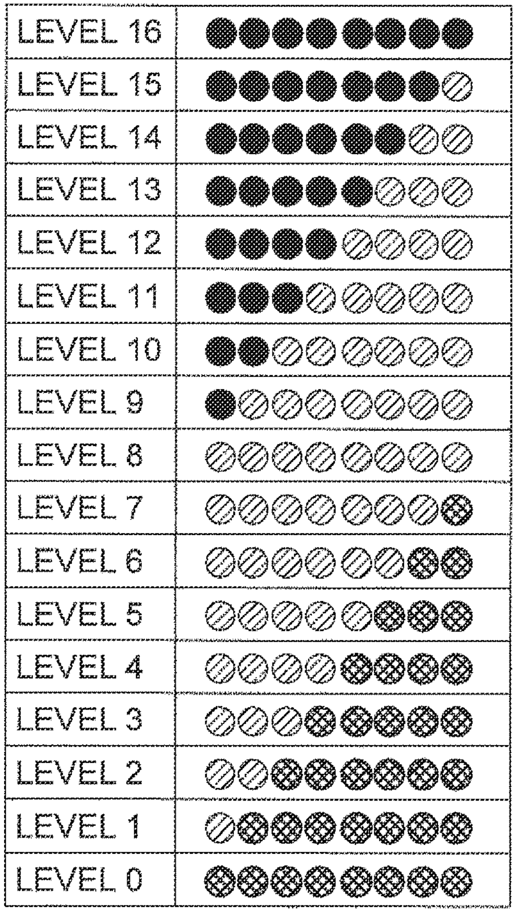

| | | | |
|---|---|---|---|
| LEVEL 16 | 1500 | 220+(80*16) | MIN. VALUE + (MAX. VALUE – MIN. VALUE) / 16 * 16 |
| LEVEL 15 | 1420 | 220+(80*15) | MIN. VALUE + (MAX. VALUE – MIN. VALUE) / 16 * 15 |
| LEVEL 14 | 1340 | 220+(80*14) | MIN. VALUE + (MAX. VALUE – MIN. VALUE) / 16 * 14 |
| LEVEL 13 | 1260 | 220+(80*13) | MIN. VALUE + (MAX. VALUE – MIN. VALUE) / 16 * 13 |
| LEVEL 12 | 1180 | 220+(80*12) | MIN. VALUE + (MAX. VALUE – MIN. VALUE) / 16 * 12 |
| LEVEL 11 | 1100 | 220+(80*11) | MIN. VALUE + (MAX. VALUE – MIN. VALUE) / 16 * 11 |
| LEVEL 10 | 1020 | 220+(80*10) | MIN. VALUE + (MAX. VALUE – MIN. VALUE) / 16 * 10 |
| LEVEL 9 | 940 | 220+(80*9) | MIN. VALUE + (MAX. VALUE – MIN. VALUE) / 16 * 9 |
| LEVEL 8 | 860 | 220+(80*8) | MIN. VALUE + (MAX. VALUE – MIN. VALUE) / 16 * 8 |
| LEVEL 7 | 780 | 220+(80*7) | MIN. VALUE + (MAX. VALUE – MIN. VALUE) / 16 * 7 |
| LEVEL 6 | 700 | 220+(80*6) | MIN. VALUE + (MAX. VALUE – MIN. VALUE) / 16 * 6 |
| LEVEL 5 | 620 | 220+(80*5) | MIN. VALUE + (MAX. VALUE – MIN. VALUE) / 16 * 5 |
| LEVEL 4 | 540 | 220+(80*4) | MIN. VALUE + (MAX. VALUE – MIN. VALUE) / 16 * 4 |
| LEVEL 3 | 460 | 220+(80*3) | MIN. VALUE + (MAX. VALUE – MIN. VALUE) / 16 * 3 |
| LEVEL 2 | 380 | 220+(80*2) | MIN. VALUE + (MAX. VALUE – MIN. VALUE) / 16 * 2 |
| LEVEL 1 | 300 | 220+(80*1) | MIN. VALUE + (MAX. VALUE – MIN. VALUE) / 16 * 1 |
| LEVEL 0 | 220 | 220+(80*0) | MIN. VALUE + (MAX. VALUE – MIN. VALUE) / 16 * 0 |

FIG. 10

METAL DETECTOR, HANDHELD POWER TOOL COMPRISING THIS METAL DETECTOR, METAL DETECTION METHOD, AND METAL DETECTION PROGRAM

CROSS-REFERENCE TO RELATED APPLICATIONS

This application claims priority to Japanese Patent Application No. 2020-209574 filed on Dec. 17, 2020. The entire disclosure of Japanese Patent Application No. 2020-209574 is hereby incorporated herein by reference.

BACKGROUND

Technical Field

The present invention relates, for example, to a metal detector that detects rebar or other such metal contained in concrete, as well as to a handheld power tool including this metal detector, a metal detection method, and a metal detection program.

Description of the Related Art

Recent years have seen the use of metal detectors that detect the position of rebar or other such metal in order to perform drilling or the like in concrete while avoiding buried targets such as rebar contained in the concrete, for example.

As one example, Patent Literature 1 discloses a probe device that makes a determination using metal detection results from a plurality of metal detectors in order to detect a wiring box disposed on the back side of a wall from the front side of the wall in a non-contact manner, notifies the user of the determination result.

CITATION LIST

Patent Literature

Patent Literature 1: JP-A 2020-60405

SUMMARY

However, the following problem is encountered with the above-mentioned conventional probe device.

With the probe device disclosed in the above publication, the presence or absence of metal is determined by using a fixed threshold value even though the arrangement, depth, size, etc., of the metal at the actual work site are not constant, so it is difficult to accurately detect the presence or absence of metal such as rebar.

More specifically, when thick rebar is continuously buried at close intervals and at a relatively shallow depth from the concrete surface, the detection results for adjacent rebar will interfere with each other, and this can make it difficult to determine the position of the rebar (wide steel plates will be mistakenly recognized as being buried).

Also, if the focus is on detecting rebar at a shallow depth, any rebar that is located more deeply may be overlooked, causing the drill bit to hit the rebar that was overlooked during a drilling operation.

Furthermore, avoiding excessive detection of rebar at a shallow depth while not overlooking rebar at deeper positions has a high degree of technical difficulty because there are countless detection conditions.

Consequently, a conventional problem was that since a highly skilled worker had to switch between a plurality of modes to detect metal, carrying out a job accurately depended on the skill level of the operator.

It is an object of the present invention to provide a metal detector capable of detecting metal contained in a target with high accuracy regardless of the skill level of the operator, as well as a handheld power tool including this metal detector, a metal detection method, and metal detection program.

The metal detector according to the first invention is a metal detector that detects metal contained in a target, including a detection signal acquisition unit, a threshold setting unit, and a determination unit. The detection signal acquisition unit acquires a detection signal which changes according to the detection intensity of the metal contained in the target, on the surface of the target. The threshold setting unit sets a threshold value used for determining the presence or absence of the metal on the basis of the maximum value and/or the minimum value included in the acquisition result for the detection signal acquired by the detection signal acquisition unit. The determination unit determines the presence or absence of the metal by using the threshold value set in the threshold value setting unit.

Here, for example, a metal detector capable of detecting rebar or other such metal contained in concrete or another such target determines whether or not rebar or other such metal is in fact contained in concrete or another such target by using a threshold value that has been set on the basis of the result of acquiring a detection signal.

Here, the target includes, for example, concrete used at a construction site such as an apartment building, a high-rise building, or a factory, a wall made of drywall, etc., and the like.

Also, the metal to be detected includes, for example, rebar contained in reinforced concrete, and metal such as aluminum or stainless steel installed in a wall.

Metal detection includes, for example, an induction type that detects the impedance of a detection coil which changes due to an eddy current generated in the metal when the metal (what is to be detected) approaches the magnetic field generated by passing a current through the detection coil; a capacitance type that detects a change in capacitance that occurs between the metal to be detected and another material; and a high-frequency oscillation method that detects a non-ferrous metal such as aluminum.

As the threshold value, for example, a threshold range may be set in which the maximum value of the detection signal that changes with the detection intensity of the metal is the upper limit threshold value and the minimum value is the lower limit threshold value, or the maximum value may be set as the upper limit threshold value, or the minimum value may be set as the lower limit threshold value.

Also, the set threshold value may be used two ways: the presence or absence of metal may be subsequently determined while updating to a new threshold value according to the magnitude of the detection signal acquired by the detection signal acquisition unit, or the initially set threshold value may be used to make the determination.

Consequently, even if the arrangement, thickness, continuity, and other such conditions of the metal in the target are different for each work site, the presence or absence of metal can be determined using a threshold value that was set on the basis of the maximum value and the minimum value of the detection signal for the metal that is actually to be detected.

This makes it possible to appropriately determine the presence or absence of metal in response to changes in various conditions, as opposed to determination of the presence or absence of metal using a fixed threshold value.

As a result, metal contained in a target can be detected with high accuracy regardless of the skill level of the operator.

The metal detector according to the second invention is the metal detector according to the first invention, wherein the threshold setting unit sets the maximum value as an upper limit threshold value and sets the minimum value as a lower limit threshold value.

Consequently, by setting a threshold range in which the maximum value of the detection signal acquired by the detection signal acquisition unit is the upper limit threshold value and the minimum value is the lower limit threshold value, it can be determined, for example, that there is metal at a position where a detection signal close to the upper limit threshold value was acquired, and that there is no metal at a position where a detection signal close to the lower limit threshold value was acquired.

The metal detector according to the third invention is the metal detector according to the first or second invention, further comprising an initialization processing unit for initializing the threshold value set in the threshold value setting unit.

Consequently, the threshold value set by the threshold value setting unit is reset (initialization processing) every time an initialization switch or the like is pressed, for example.

This allows the threshold value to be initialized by operating the initialization switch every time the work site changes, for example, so a threshold value newly set for each site can be used to determine the presence or absence of metal more accurately.

The metal detector according to the fourth invention is the metal detector according to any of the first to third inventions, further comprising a memory unit that stores the threshold values set by the threshold value setting unit.

Consequently, by storing the threshold valued set by the threshold value setting unit, the presence or absence of metal can be determined by using that threshold value until a new threshold value is set, for example.

The metal detector according to the fifth invention is the metal detector according to the fourth invention, further comprising a threshold value updating unit that updates the threshold value stored in the memory unit according to the acquisition result for the detection signal in the detection signal acquisition unit.

Consequently, when the detection signal is acquired while moving along the surface of a target such as concrete, and a maximum value larger than the threshold value stored in the memory unit, or a minimum value smaller than the threshold value, is acquired, this can be updated as the new threshold.

As a result, the presence or absence of metal can be determined by using the newly set updated threshold value, for example.

The metal detector according to the sixth invention is the metal detector according to the fifth invention, wherein the threshold value updating unit repeatedly updates the threshold value during one scan of the target.

Consequently, during one scan for detecting metal while moving along the surface of a target such as concrete, a threshold value for determination that was set on the basis of the maximum value and/or the minimum value of the detection signal is repeatedly updated on the basis of the value of the newly acquired detection signal, and the presence or absence of metal can be determined using this updated threshold value.

The metal detector according to the seventh invention is a metal detector according to any of the first to sixth inventions, further comprising a display unit that displays the metal detection result, and a display control unit that controls the display unit.

This makes it possible to control so that the determination result based on a determination using the set threshold value is displayed on the display unit.

Consequently, the operator can recognize the presence or absence of metal in the target by checking the color of the light displayed on the display unit, text information, or the like.

The metal detector according to the eighth invention is the metal detector according to the seventh invention, wherein the display control unit controls the display unit so as to display light of different colors according to the detection intensity for the metal.

Consequently, when it is determined that there is metal, for example, a red light comes on, and when it is determined that there is no metal, a green light comes on, which allows the operator to recognize the presence or absence of metal in the target simply by checking the color of the lit light.

The metal detector according to the ninth invention is the metal detector according to the seventh or eighth invention, further comprising a level setting unit that sets a plurality of levels obtained by dividing up the level between the maximum value and the minimum value of the detection signal acquired by the detection signal acquisition unit at specific intervals. The display control unit performs control so as to switch the color of the light displayed on the display unit according to the plurality of levels set in the level setting unit.

Consequently, light of a plurality of different colors can be displayed according to the plurality of levels set by dividing up the level between the maximum value and the minimum value of the detection signal, and this allows the operator to carry out the work properly while estimating the distance from the metal detector to the metal on the basis of the color of light on the display unit.

The metal detector according to the tenth invention is the metal detector according to any of the first to ninth inventions, further comprising a contact detection unit that detects contact with the target.

Consequently, by detecting that the metal detector has come into contact with a target such as concrete, it is possible to perform control such as prohibiting the driving of the drive unit of a handheld power tool unless the metal detector is in contact with the target.

The metal detector according to the eleventh invention is the metal detector according to the tenth invention, wherein the contact detection unit is a contact switch that changes from an OFF state to an ON state upon coming into contact with the target.

Consequently, by using a pressing type of contact switch as the contact detection unit, for example, it is possible to detect that the metal detector has come into contact with the target, with an inexpensive configuration.

The metal detector according to the twelfth invention is the metal detector according to the tenth or eleventh invention, further comprising a retracting mechanism that is attached to the distal end of a handheld power tool which works the target, and that retracts from the distal end of the handheld power tool when the contact detection unit detects contact with the target.

Here, the handheld power tool to which the metal detector is mounted includes power tools that perform various kinds of work on concrete or another such target while being held by an operator, such as a hammer drill, an impact drill, and a vibrating drill.

Consequently, if it is detected that the metal detector has come into contact with a target in a state in which the metal detector is attached to the distal end of a handheld power tool, the metal detector is automatically retracted from the distal end of the handheld power tool, which makes it easier for the operator to see the portion to be worked, for example, and makes it less likely that any dust or the like produced when the tip tool of the drill, etc., is rotated to drill a hole will cling to the metal detector.

The metal detector according to the thirteenth invention is the metal detector according to any of the first to twelfth inventions, wherein the metal detector is removably attached to a handheld power tool that works the target.

Consequently, a metal detector mounted on a handheld power tool can be used in a state in which it can be attached to and detached from the main body, so that the metal detector can be attached or detached as needed.

The handheld power tool according to the fourteenth invention comprises the metal detector according to any of claims 1 to 13, a main body to which the metal detector is mounted, a drive unit that is provided to the main body and drives an attached distal end tool, and a drive control unit that is provided to the main body and controls the drive unit.

Consequently, the handheld power tool can be used in a state in which the above-mentioned metal detector is attached, which allows the target to undergo various kinds of work while the operator is notified of the presence or absence of metal, without coming into contact with the metal within the concrete or other such target.

The handheld power tool according to the fifteenth invention is the handheld power tool according to the fourteenth invention, wherein the drive control unit prohibits the drive of the drive unit when the determination unit has determined that metal is present.

Consequently, if the determination unit determines that there is metal, this determination result can be reflected in the drive control of the drive unit to prohibit drive.

This avoids problems such as when the tip of the drill comes into contact with metal in the course of drilling or the like even though it has been determined that there is metal present, which further improves safety.

The handheld power tool according to the sixteenth invention is the handheld power tool according to the fourteenth or fifteenth invention, wherein the drive control unit permits the drive of the drive unit when the determination unit has determined that there is no metal.

Consequently, if the determination unit determines that there is no metal, this determination result can be reflected in the drive control of the drive unit to allow drive.

This avoids problems such as when the tip of the drill comes into contact with metal in the course of drilling or the like even though it has been determined that there is metal present, which further improves safety.

The metal detection method according to the seventeenth invention is a metal detection method that makes use of a metal detector that detects metal contained in a target, the method comprising a detection signal acquisition step, a threshold setting step, and a determination step. In the detection signal acquisition step, the detection signal acquisition unit of the metal detector acquires a detection signal that changes according to the detection intensity for the metal contained in the target, on the surface of the target. In the threshold setting step, the threshold value setting unit of the metal detector sets a threshold value that is used to determine the presence or absence of the metal, on the basis of the maximum value and/or the minimum value included in the acquisition results for the detection signal acquired in the detection signal acquisition step. In the determination step, the determination unit of the metal detector determines the presence or absence of metal by using the threshold value set in the threshold value setting step.

Here, in a metal detection method using a metal detector capable of detecting metal such as rebar contained in a target such as concrete, for example, the presence or absence of rebar or other such metal contained in the concrete or other such target is determined using a threshold value set on the basis of the acquisition result for the detection signal.

Here, the target includes, for example, concrete used at a construction site such as an apartment building, a high-rise building, or a factory, a wall made of drywall, etc., and the like.

Also, the metal to be detected includes, for example, rebar contained in reinforced concrete, and metal such as aluminum or stainless steel installed in a wall.

Metal detection includes, for example, an induction type that detects the impedance of a detection coil which changes due to an eddy current generated in the metal when the metal (what is to be detected) approaches the magnetic field generated by passing a current through the detection coil; a capacitance type that detects a change in capacitance that occurs between the metal to be detected and another material; and a high-frequency oscillation method that detects a non-ferrous metal such as aluminum.

As the threshold value, for example, a threshold range may be set in which the maximum value of the detection signal that changes with the detection intensity of the metal is the upper limit threshold value and the minimum value is the lower limit threshold value, or the maximum value may be set as the upper limit threshold value, or the minimum value may be set as the lower limit threshold value.

Also, the set threshold value may be used two ways: the presence or absence of metal may be subsequently determined while updating to a new threshold value according to the magnitude of the detection signal acquired by the detection signal acquisition unit, or the initially set threshold value may be used to make the determination.

Consequently, even if the arrangement, thickness, continuity, and other such conditions of the metal in the target are different for each work site, the presence or absence of metal can be determined using a threshold value that was set on the basis of the maximum value and the minimum value of the detection signal for the metal that is actually to be detected.

This makes it possible to appropriately determine the presence or absence of metal in response to changes in various conditions, as opposed to determination of the presence or absence of metal using a fixed threshold value.

As a result, metal contained in a target can be detected with high accuracy regardless of the skill level of the operator.

The metal detection program according to the eighteenth invention is a metal detection program for a metal detector that detects metal contained in a target, the metal detection program causing a computer to execute a metal detection method comprising a detection signal acquisition step, a threshold setting step, and a determination step. In the detection signal acquisition step, the detection signal acquisition unit of the metal detector acquires a detection signal that changes according to the detection intensity for the metal contained in the target, on the surface of the target. In the threshold setting step, the threshold value setting unit of the metal detector sets a threshold value that is used to determine the presence or absence of the metal on the basis of the maximum value and/or the minimum value included in the acquisition results for the detection signal acquired in the detection signal acquisition step. In the determination step, the determination unit of the metal detector determines the presence or absence of the metal by using the threshold value set in the threshold value setting step.

Here, for example, in a metal detection program of a metal detector capable of detecting metal such as rebar contained in a target such as concrete, the presence or absence of rebar or other such metal contained in the concrete or other such target is determined using a threshold value set on the basis of the acquisition result for the detection signal.

Here, the target includes, for example, concrete used at a construction site such as an apartment building, a high-rise building, or a factory, a wall made of drywall, etc., and the like.

Also, the metal to be detected includes, for example, rebar contained in reinforced concrete, and metal such as aluminum or stainless steel installed in a wall. Metal detection includes, for example, an induction type that detects the impedance of a detection coil which changes due to an eddy current generated in the metal when the metal (what is to be detected) approaches the magnetic field generated by passing a current through the detection coil; a capacitance type that detects a change in capacitance that occurs between the metal to be detected and another material; and a high-frequency oscillation method that detects a non-ferrous metal such as aluminum.

As the threshold value, for example, a threshold range may be set in which the maximum value of the detection signal that changes with the detection intensity of the metal is the upper limit threshold value and the minimum value is the lower limit threshold value, or the maximum value may be set as the upper limit threshold value, or the minimum value may be set as the lower limit threshold value.

Also, the set threshold value may be used two ways: the presence or absence of metal may be subsequently determined while updating to a new threshold value according to the magnitude of the detection signal acquired by the detection signal acquisition unit, or the initially set threshold value may be used to make the determination.

Consequently, even if the arrangement, thickness, continuity, and other such conditions of the metal in the target are different for each work site, the presence or absence of metal can be determined using a threshold value that was set on the basis of the maximum value and the minimum value of the detection signal for the metal that is actually to be detected.

This makes it possible to appropriately determine the presence or absence of metal in response to changes in various conditions, as opposed to determination of the presence or absence of metal using a fixed threshold value.

As a result, metal contained in a target can be detected with high accuracy regardless of the skill level of the operator.

Effects

With to the metal detector according to the present invention, metal contained in a target can be detected with high accuracy regardless of the skill level of the operator.

BRIEF DESCRIPTION OF THE DRAWINGS

FIG. 10 is a diagram showing a level table set by a level setting unit included in the metal detector in FIG. 6;

DETAILED DESCRIPTION

Embodiment 1

A handheld power tool 10 including a metal detector 20 according to an embodiment of the present invention will now be described with reference to FIGS. 1 to 19 and FIG. 25.

In the following description, the distal end side means the side on which a tip tool 18*a* for machining with the handheld power tool 10 is mounted, and the rear end side means the opposite side from the distal end side.

Figure 1:
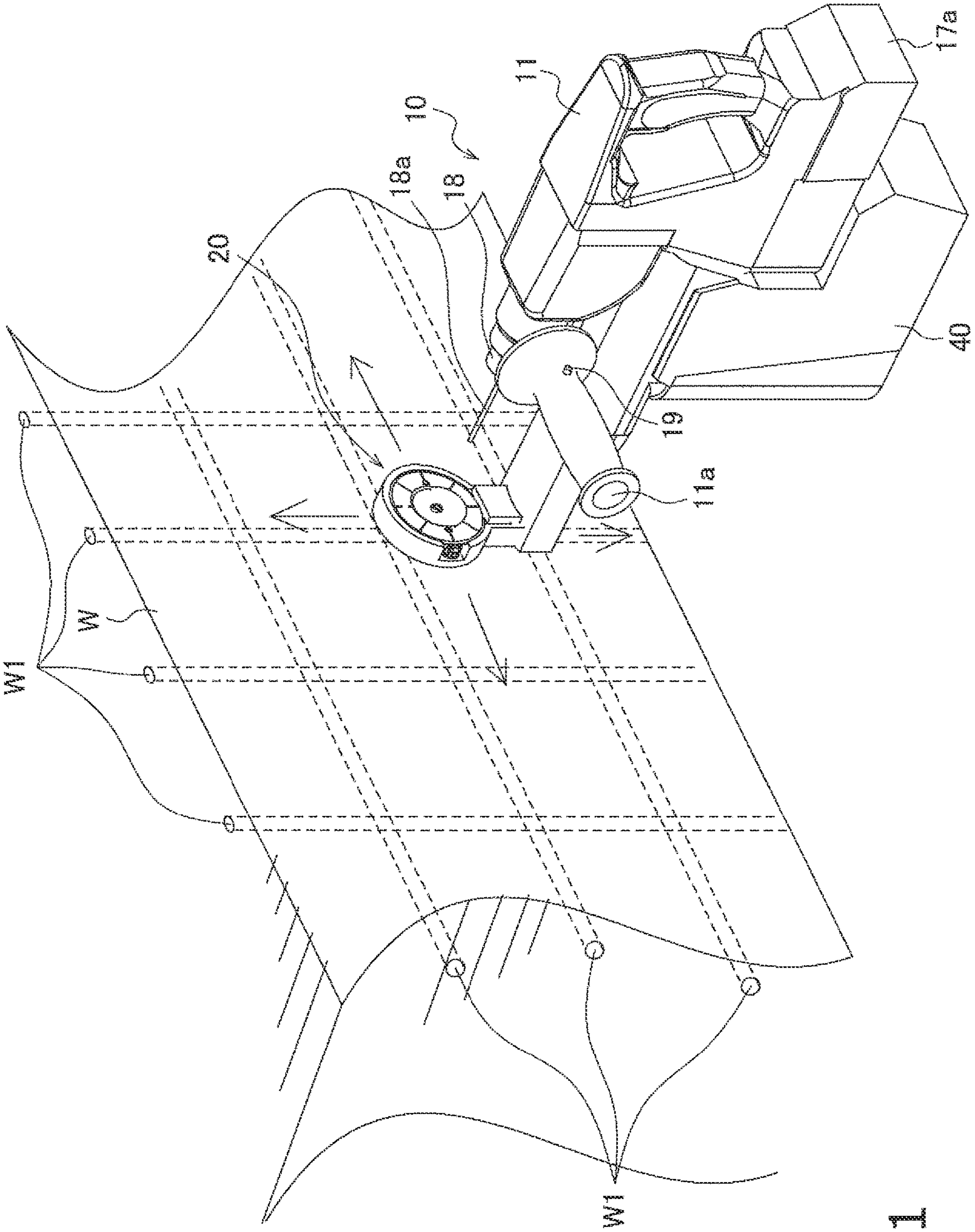
FIG. 1 is an oblique view of a state in which concrete is worked with a handheld power tool equipped with the metal detector according to an embodiment of the present invention, while the presence or absence of rebar is detected.

As shown in FIG. 1, the handheld power tool 10 according to this embodiment is, for example, a hammer drill (a type of handheld power tool) for performing work while the position of rebar (metal) embedded in the concrete (target) W is detected in a state in which the tool is being held by the operator, the metal detector 20 is integrally attached on the tip portion 18 side to which a tip tool 18*a* such as a drill has been mounted.

As shown in FIG. 1, the handheld power tool 10 moves the metal detector 20 over the surface of the concrete W, and when the position where the rebar W1 is embedded is approached, the operator is notified of the presence or absence of the rebar W1 by changing the color of the light that appears on a display unit 24 (see FIG. 6 and the like; discussed below).

Consequently, the operator can recognize the presence or absence of the rebar W1 by looking at the color of the light on the display unit 24. This allows drilling or other such work to be performed on the concrete W with the handheld power tool 10 while avoiding contact of the tip tool 18*a* with the rebar W1.

In this embodiment, an example is given in which a plurality of rebars W1 are embedded in the concrete W in a grid pattern, but the number, thickness, length, etc., of the rebar W1 are not limited to what is shown in FIG. 1.

Here, first, the outward configuration of the handheld power tool 10 will be described with reference to FIGS. 2 to 5.

Figure 2:
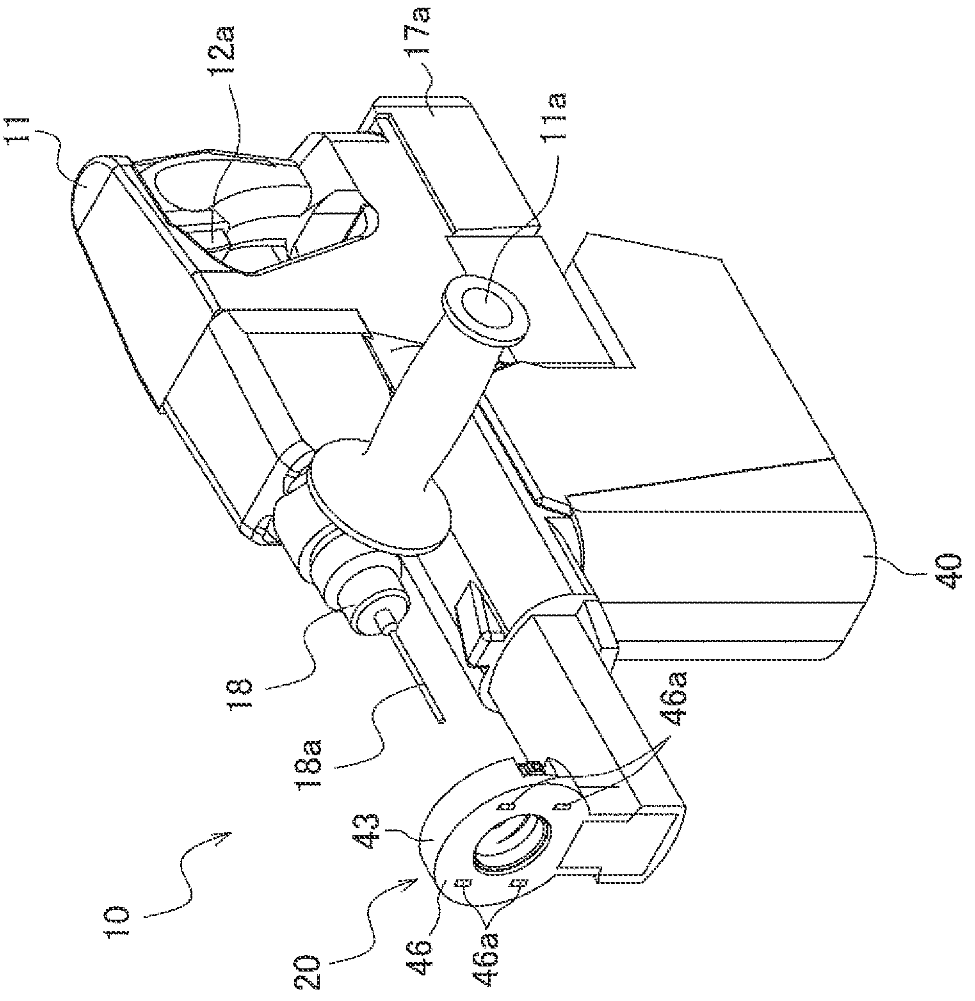
FIG. 2 is an overall oblique view of the configuration of the handheld power tool in FIG. 1.
Figure 3:
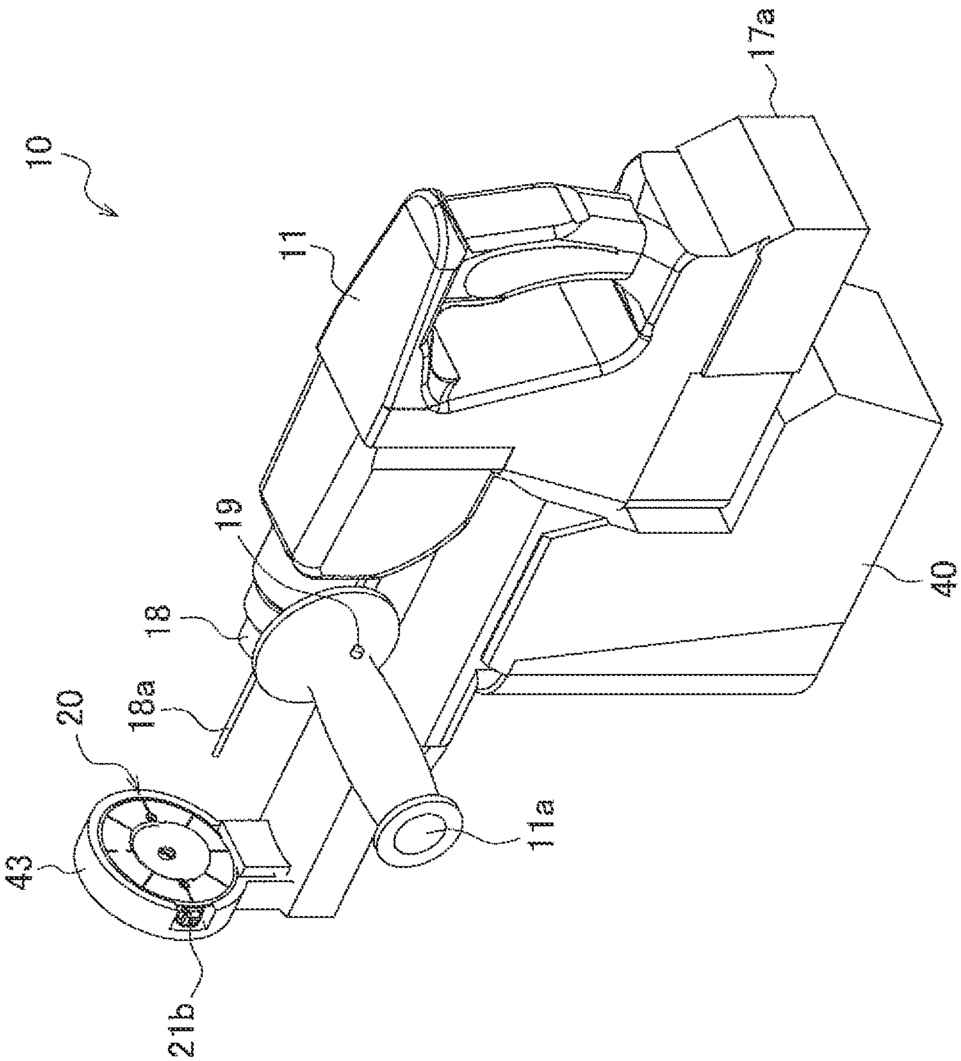
FIG. 3 is an overall oblique view of the configuration of the handheld power tool in FIG. 2.

As shown in FIGS. 2 and 3, the handheld power tool 10 includes a main body 11, the metal detector 20, and a dust collecting unit 40.

The main body 11 has a grip portion 11*a* that is gripped by an operator during work, a trigger switch 12*a* that rotationally drives a motor (drive unit) 14 (see FIG. 8) when gripped by the operator, a battery 17*a* that supplies the electric power for the handheld power tool 10, and a tip portion 18 that is disposed on the side that does the work on the concrete W.

As shown in FIGS. 2 and 3, the grip portion 11*a* is provided so as to project from the left side surface of the main body 11, and is gripped by the left hand of the operator when performing work with the handheld power tool 10.

The grip portion 11*a* may be attached to the operator on the opposite side depending on the dominant hand of the operator.

Also, as shown in FIG. 3, a reset switch 19, which is pressed when the metal detector 20 is manually initialized, is provided on the front of the grip portion 11*a*.

As shown in FIG. 2, the trigger switch 12*a* is provided on the opposite side from the tip portion 18 (the rear end side) of the main body 11, and when the tip tool 18*a* is rotated to perform the work, this switch is gripped by the operator.

The battery 17*a* is a rechargeable secondary battery that supplies power to the components included in the handheld power tool 10, and is attached, so as to be replaceable, at the lower portion of the main body 11 on the rear end side, as shown in FIGS. 2 and 3.

As shown in FIGS. 2 and 3, the tip portion 18 is provided on the side of the main body 11 closer to the concrete W during work, and a tip tool 18*a* such as a drill is attached to the tip portion 18. The tip portion 18 is rotationally driven along with the tip tool 18*a* by controlling the rotational drive of the motor 14 according to how much the trigger switch 12*a* is operated.

Figure 4:
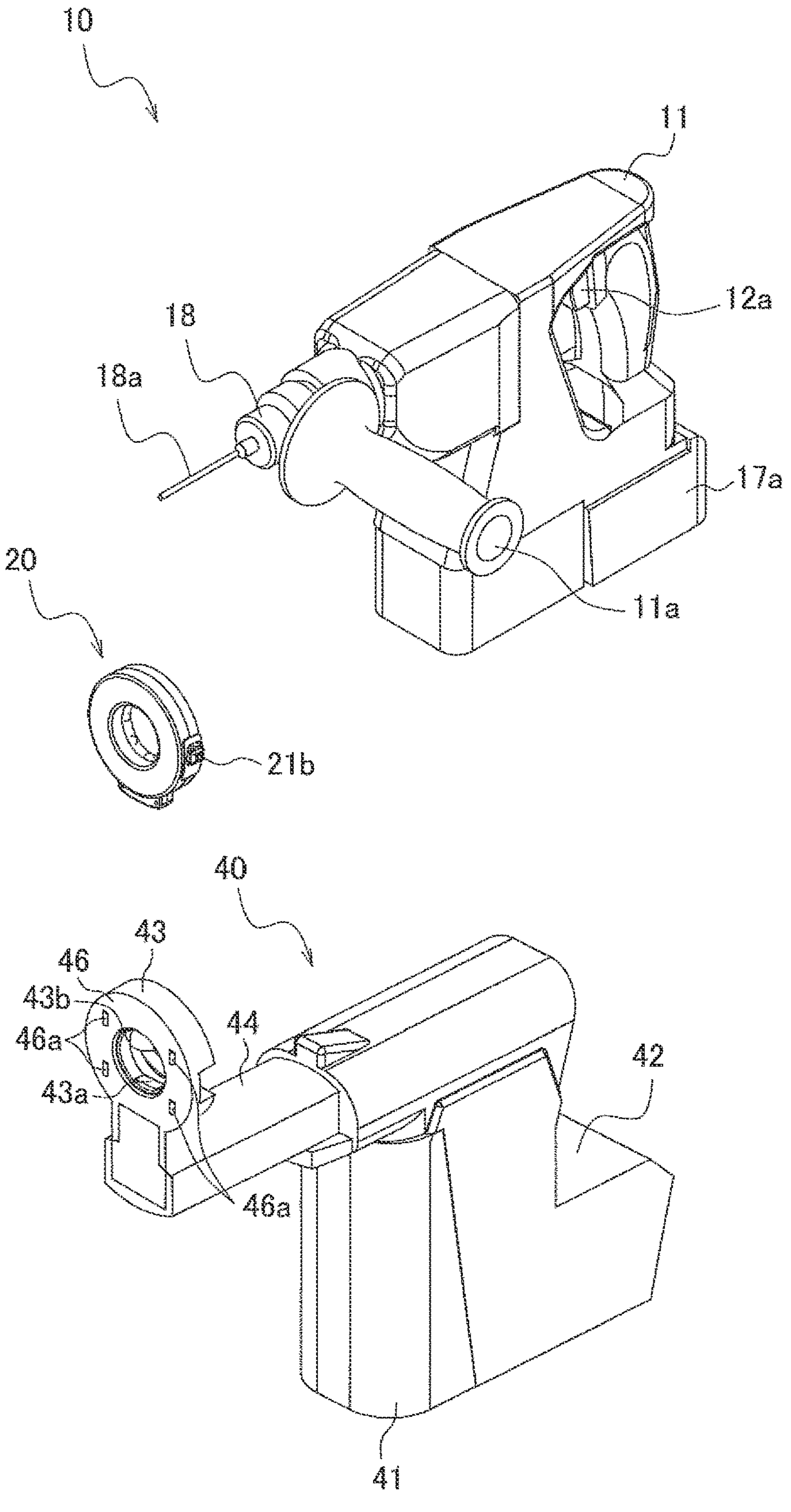
FIG. 4 is an exploded oblique view of the handheld power tool in FIG. 2.
Figure 5:
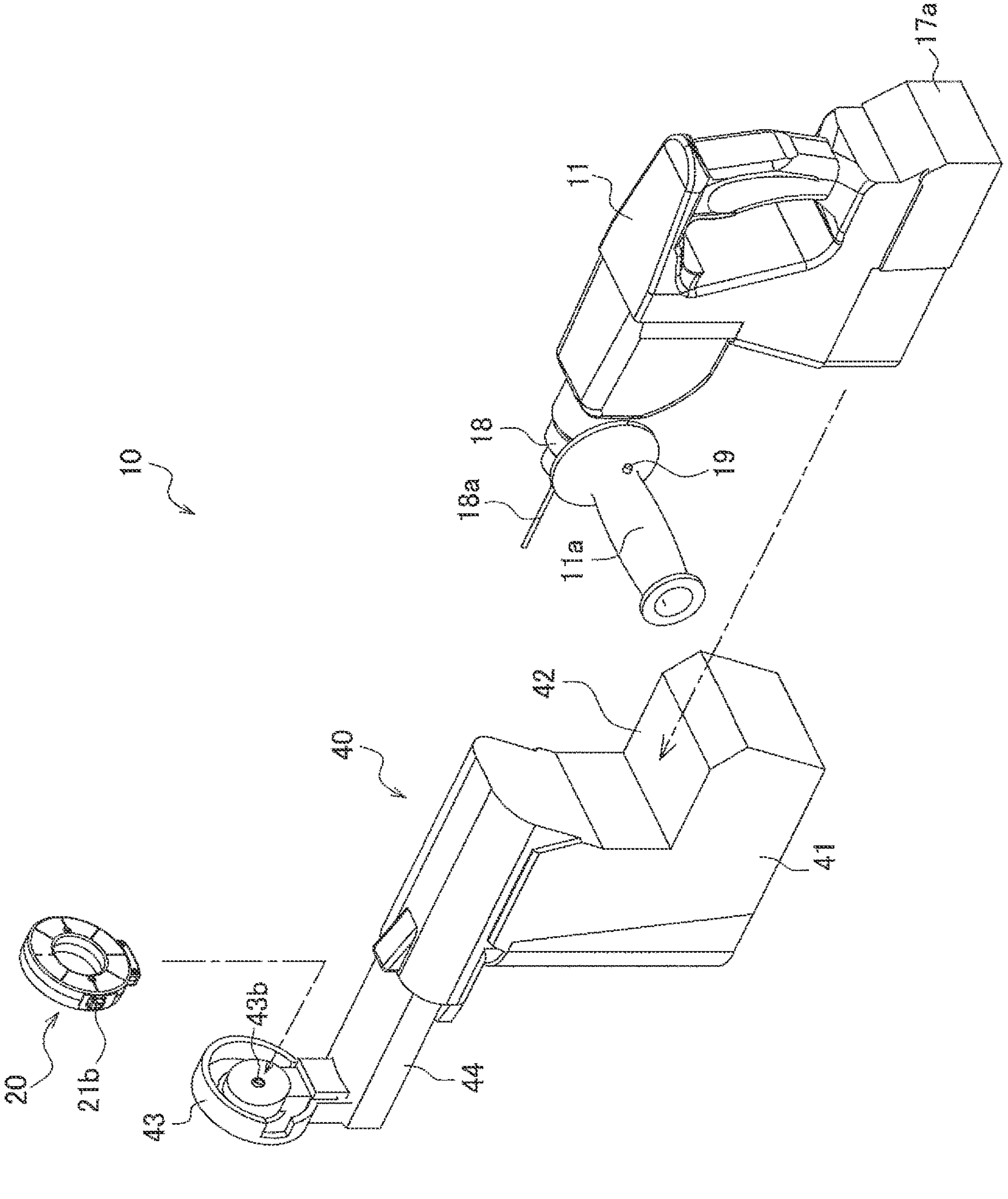
FIG. 5 is an exploded oblique view of the handheld power tool in FIG. 3.

The metal detector 20 is attached in an integrated state on the distal end side of the main body 11 of the handheld power tool 10 in order to detect the presence or absence of the rebar W1 in the concrete W on which work such as drilling is to be performed with the handheld power tool 10. As shown in FIGS. 4 and 5, the metal detector 20 is removably attached to a recess formed on the rear end side of a detector attachment unit 43 of the dust collecting unit 40.

The metal detector 20 has a substantially annular shape, and a work hole, into which the tip tool 18*a* such as a drill is inserted during machining, is provided in the central portion thereof.

The configuration of the metal detector 20 will be described in detail below.

The dust collecting unit 40 is provided for sucking up the dust of the concrete W produced when the tip tool 18*a* such as a drill is rotationally driven to drill a hole in the concrete W, for example. More specifically, dust and the like are sucked up through a suction port 43*a* provided to the detector attachment unit 43, which is where the metal detector 20 is mounted at a position on the distal end side of the handheld power tool 10.

As shown in FIGS. 4 and 5, the dust collecting unit 40 is removably attached to the lower part of the main body 11 of the handheld power tool 10, and has a main body 41, a mounting unit 42, the detector attachment unit 43, and an arm portion 44.

The main body 41 has a boxy shape including a suction mechanism (not shown) inside, and a space is formed for collecting dust and the like sucked in through the suction port 43*a* via the arm portion 44. The main body 41 is provided with the detector attachment unit 43 and the arm portion 44 on the front end side where work is performed, and with the mounting unit 42 on the rear end side.

As shown in FIG. 5, the mounting unit 42 is the portion of the handheld power tool 10 to which the main body 11 is mounted, and is fixed in a state of being engaged with the main body 11.

As shown in FIGS. 4 and 5, the detector attachment unit 43 is a substantially annular portion provided at the distal end of the arm portion 44 provided on the distal end side of the main body 41 of the dust collecting unit 40, and the metal detector 20 is attached from the rear end side. The detector attachment unit 43 has the suction port 43*a* formed in the inner peripheral surface of a substantially annular portion.

The detector attachment unit 43 also has an opening 43*b*, which serves as a work hole into which the tip tool 18*a* such as a drill is inserted, in the central portion of the substantially annular ring.

Furthermore, a contact surface 46 (see FIG. 2), which comes into contact with the concrete W during the work of detecting the rebar W1 with the metal detector 20, is formed on the distal end side of the detector attachment unit 43.

As shown in FIG. 2, four rollers 46*a* are rotatably attached to the contact surface 46 so as to surround the central opening (work hole) of the detector attachment unit 43.

Consequently, the metal detector 20 can be smoothly moved in the scanning direction (for example, the lateral direction) in a state in which the contact surface 46 is in contact with the surface of the concrete W. This allows metal detection to be performed while moving the metal detector 20 (handheld power tool 10) in the desired scanning direction without producing frictional resistance between the surface of the concrete W and the contact surface 46.

The arm portion 44 is a member that is hollow inside, and guides dust and the like sucked up through the suction port 43*a* of the detector attachment unit 43 provided on the distal end side into the main body 41. Also, the arm portion 44 is attached to the main body 41 in a state that allows its movement forward and backward.

This allows the length of the arm portion 44 to be adjusted such that the length will be appropriate for the length of the tip tool 18*a* mounted on the tip portion 18, for example. Also, when only the work of detecting the presence or absence of the rebar W1 with the metal detector 20 is performed before drilling or other such work, or when the tip tool 18*a* is attached to or detached from the tip portion 18, etc., the work of detecting the rebar W1 and the work of replacing the tip tool 18*a* can be performed more easily by pulling out the arm portion 44 from the main body 41.

Next, the configuration of the metal detector 20 will be described with reference to FIG. 6.

Figure 6:
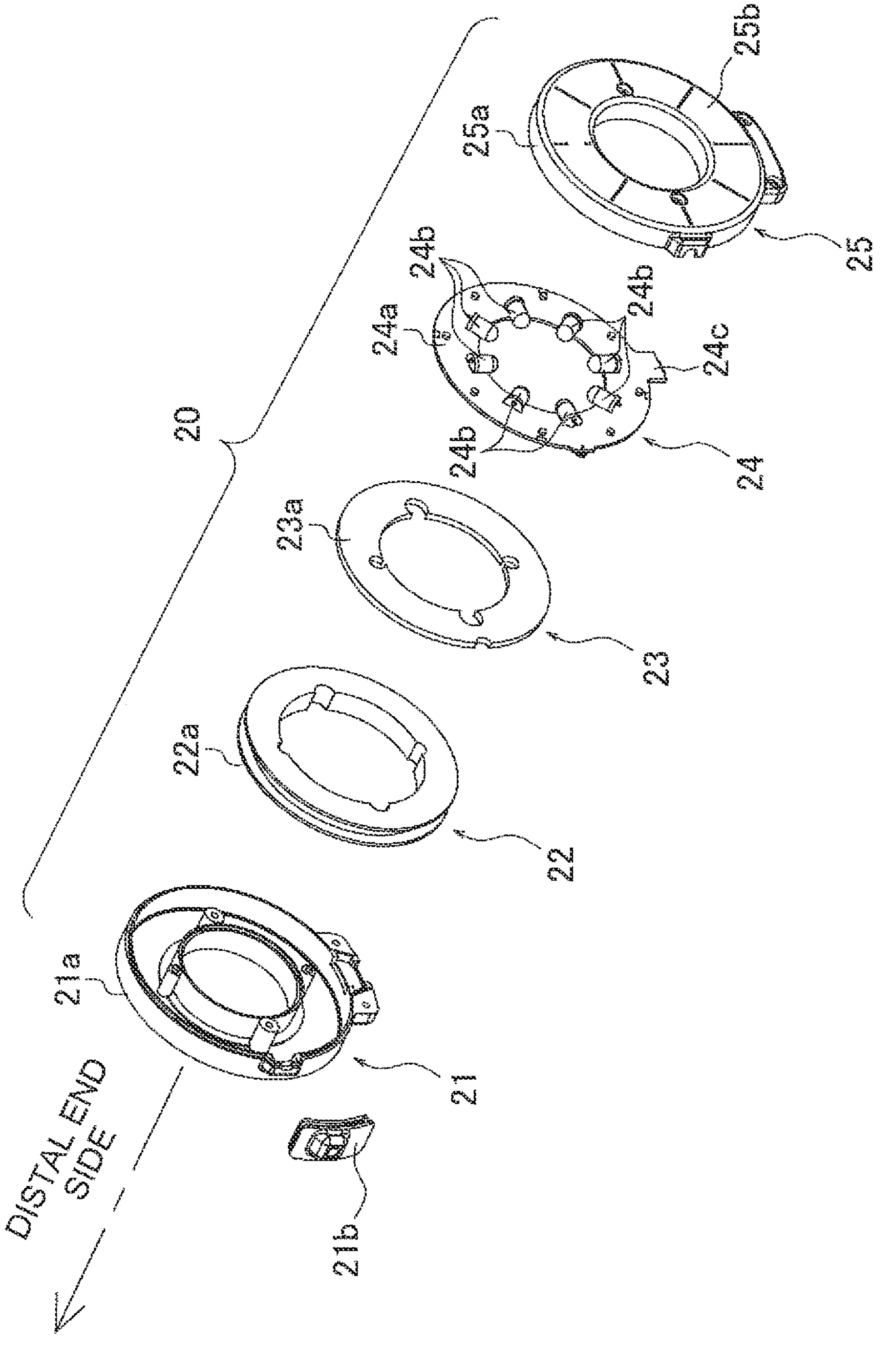
FIG. 6 is an exploded oblique view of the configuration of the metal detector provided to the handheld power tool in FIG. 2, etc.

As shown in FIG. 6, the metal detector 20 has a substantially annular shape, and has a case (mounting unit) 21, a detector unit 22, a spacer 23, a display unit 24, and a cover 25.

As shown in FIG. 5, the case (mounting unit) 21 is disposed on the side where the metal detector 20 is mounted in the recess of the detector attachment unit 43. As shown in FIG. 6, the case 21 is a substantially annular member disposed on the most distal end side among the members constituting the metal detector 20, and has a main body 21*a* and a switch cover 21*b*.

The main body 21*a* is a substantially annular member having an opening in the center, and includes the detector unit 22, the spacer 23, and the display unit 24 in a space formed between the main body 21*a* and the cover 25.

The switch cover 21*b* is, for example, a rubber member that is attached to the outer peripheral surface of the main body 21*a*, and forms a dust-proof and drip-proof structure that covers an initialization switch (not shown), etc., provided inside the main body 21*a*.

Then, when a portion of the switch cover 21*b* is pressed, the detection signal of the metal detector 20 can be initialized.

As shown in FIG. 6, the detector unit 22 has a substantially annular main body 22*a* and a coil 22*b* that is wound around the outer peripheral surface of the main body 22*a*. The detector unit 22 is an induction type that detects the rebar W1 by sensing the impedance of a coil, which changes due to the eddy current generated in the rebar W1 when the rebar W1 approaches the magnetic field formed when a current is passed through the coil 22*b*.

As shown in FIG. 6, the spacer 23 has a substantially annular main body 23*a*, and is provided between the detector unit 22 and the substrate 24*a* of the display unit 24.

Consequently, the spacer 23 can reduce the metal influence of the substrate 24*a* on the detector unit 22, and make it less likely that heat generated in the substrate 24*a* will be transferred to the detector unit 22.

As shown in FIG. 6, the display unit 24 has a substrate 24*a*, eight full-color LEDs (light emitting diodes) 24*b*, and a USB (universal serial bus) connector 24*c*. The eight full-color LEDs 24*b* are disposed on the substantially annular substrate 24*a*, facing toward the opening formed in the center of the substrate 24*a*. The LEDs 24*b* notify the operator of the detection result for the rebar W1 detected by the detector unit 22, by turning on lights of different colors (green, yellow, and red in this embodiment) according to the distance to the rebar W1.

For instance, if the distance to the rebar W1 is relatively long, the display unit 24 lights the LEDs 24*b* with green light. On the other hand, if the distance to the rebar W1 is relatively short, the display unit 24 lights the LEDs 24*b* with red light. Furthermore, if the distance to the rebar W1 is between when the green and red lights are lit, the display unit 24 causes the LEDs 24*b* to emit yellow light.

With the metal detector 20 in this embodiment, since the display unit 24 includes eight LEDs 24*b*, all eight LEDs 24*b* may be lit in the same lighting color, or the numbers of green, yellow, and red lights may be switched depending on the distance to the rebar W1.

Consequently, the operator can recognize the approximate distance to the rebar W1 by checking the color of the lights on the display unit 24 of the metal detector 20.

Furthermore, with the metal detector 20 in this embodiment, if it is determined that there is no rebar W1 as a result of detection by the detector unit 22, for example, it is detected that the trigger switch 12*a* has been operated after the LEDs 24*b* are lit in green, and the LEDs 24*b* are lit in white.

This white light is used as auxiliary light that brightly illuminates the position where work is to be performed when the trigger switch 12*a* is operated to rotate the motor 14 and the tip tool 18*a* is rotationally driven.

Consequently, the display unit 24 can not only show the detection result of the rebar W1 but also turn on an auxiliary light that brightly illuminates the work position when the work is being performed.

Figure 25:
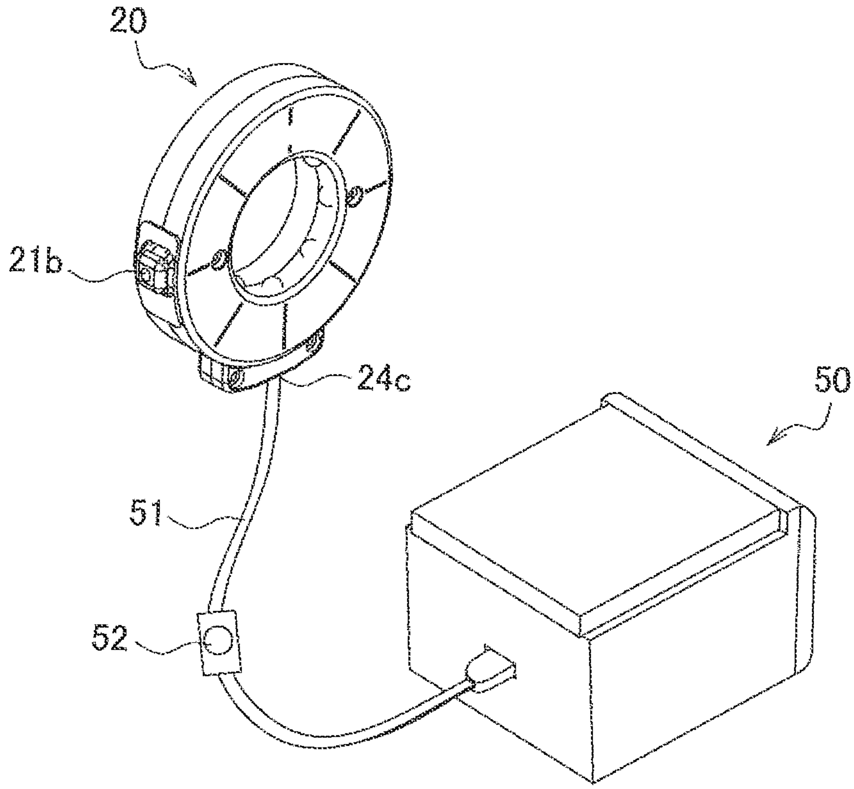
FIG. 25 is an oblique view of a state in which the metal detector in FIG. 6 is used alone.

As shown in FIG. 25, one end of a USB cable 51 for connecting to an external device such as a battery 50 is connected to the USB connector 24*c*. As a result, the metal detector 20 can be used alone by receiving power from the battery 50 to which the other end of the USB cable 51 is connected.

As shown in FIG. 25, the USB cable 51 may be provided with an initialization switch 52 near the middle of the cable. As a result, the initialization processing of the metal detector 20 can also be performed when the initialization switch 52 provided on the USB cable 51 is operated.

As shown in FIG. 6, the cover 25 is a substantially annular member that is disposed on the rearmost end side among the members constituting the metal detector 20, and together with the above-mentioned case 21, constitutes the outer shell of the metal detector 20. The cover 25 also has a main body 25*a* and a mode display surface 25*b*.

The main body 25*a* is a substantially annular member, and three LEDs used for mode notification (not shown) are mounted in the interior thereof.

The mode display surface 25*b* is a surface on the rear end side (operator side) of the main body 25*a*, and displays a plurality of metal detection modes (discussed below) by turning on lights of different colors.

Figure 7:
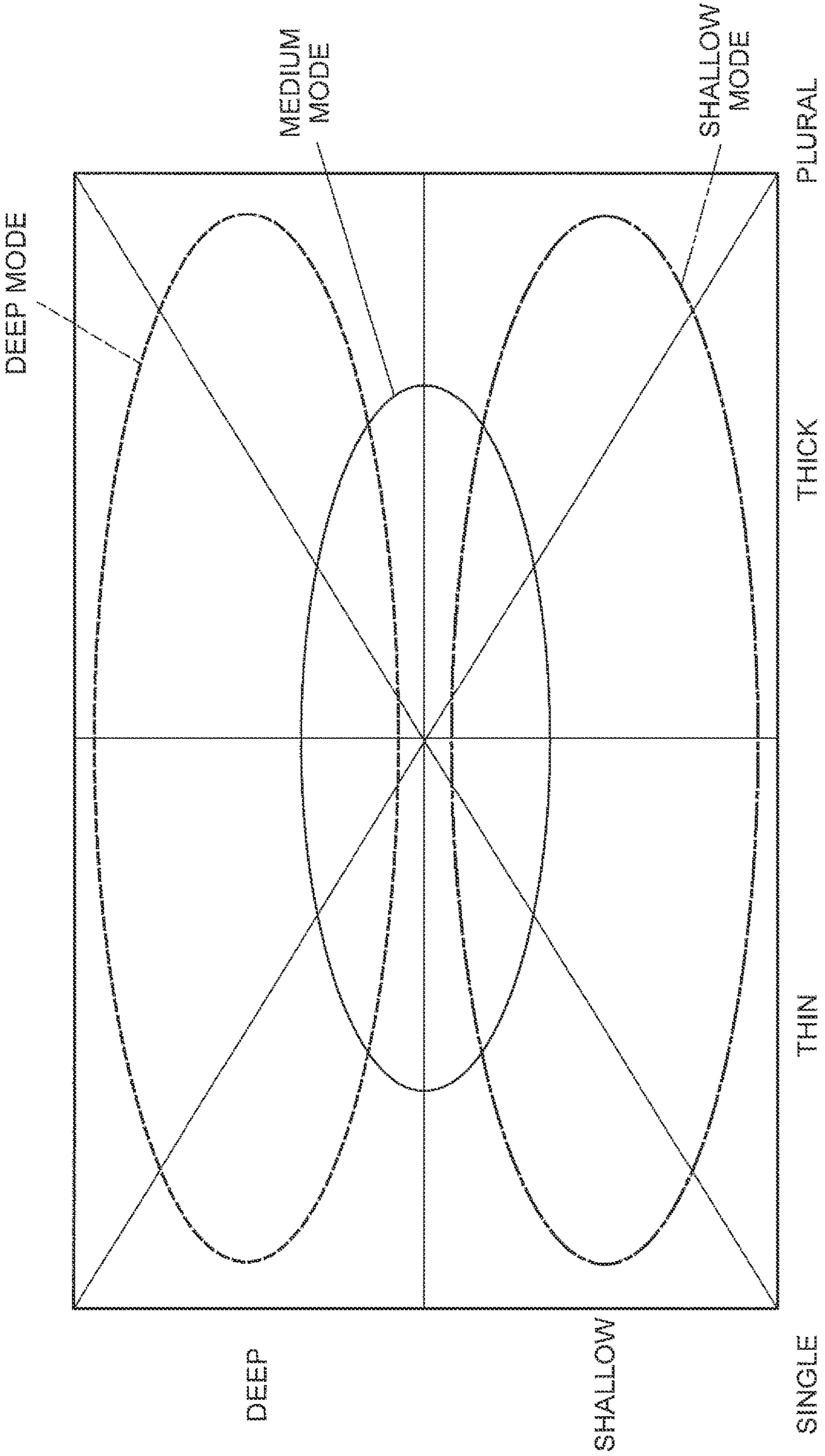
FIG. 7 is a graph of the metal detection modes that can be set in the handheld power tool in FIG. 2, etc.

Here, in this embodiment, as shown in FIG. 7, three metal detection modes (deep mode, medium mode, and shallow mode) selected in advance by the operator are set.

In the three metal detection modes, different threshold values for determination are set according to, for example, the depth at which the rebar W1 is thought to exist, the thickness of the rebar W1, the number of rebars, the spacing, and so forth, and the mode is selected by the operator. Switching between these three modes is performed with a mode switch (not shown).

Since a different threshold value is thus set for each mode, if the shallow mode is selected, for example, it is possible to improve the detection accuracy for the rebar W1 located at a relatively shallow depth from the surface of the concrete W. This allows a plurality of thick rebars W1 located at a relatively shallow depth from the surface of the concrete W to be detected with high accuracy, for example.

Also, when the deep mode is selected, the detection accuracy of the rebar W1 located at a relatively deep position from the surface of the concrete W can be improved. This allows for better accuracy in detecting thin rebar W1 located at a greater depth from the surface of the concrete W, for example.

The control blocks of the handheld power tool 10 will now be described with reference to FIG. 8.

As described above, the handheld power tool 10 includes the main body 11, the metal detector 20, and the dust collecting unit 40.

Figure 8:
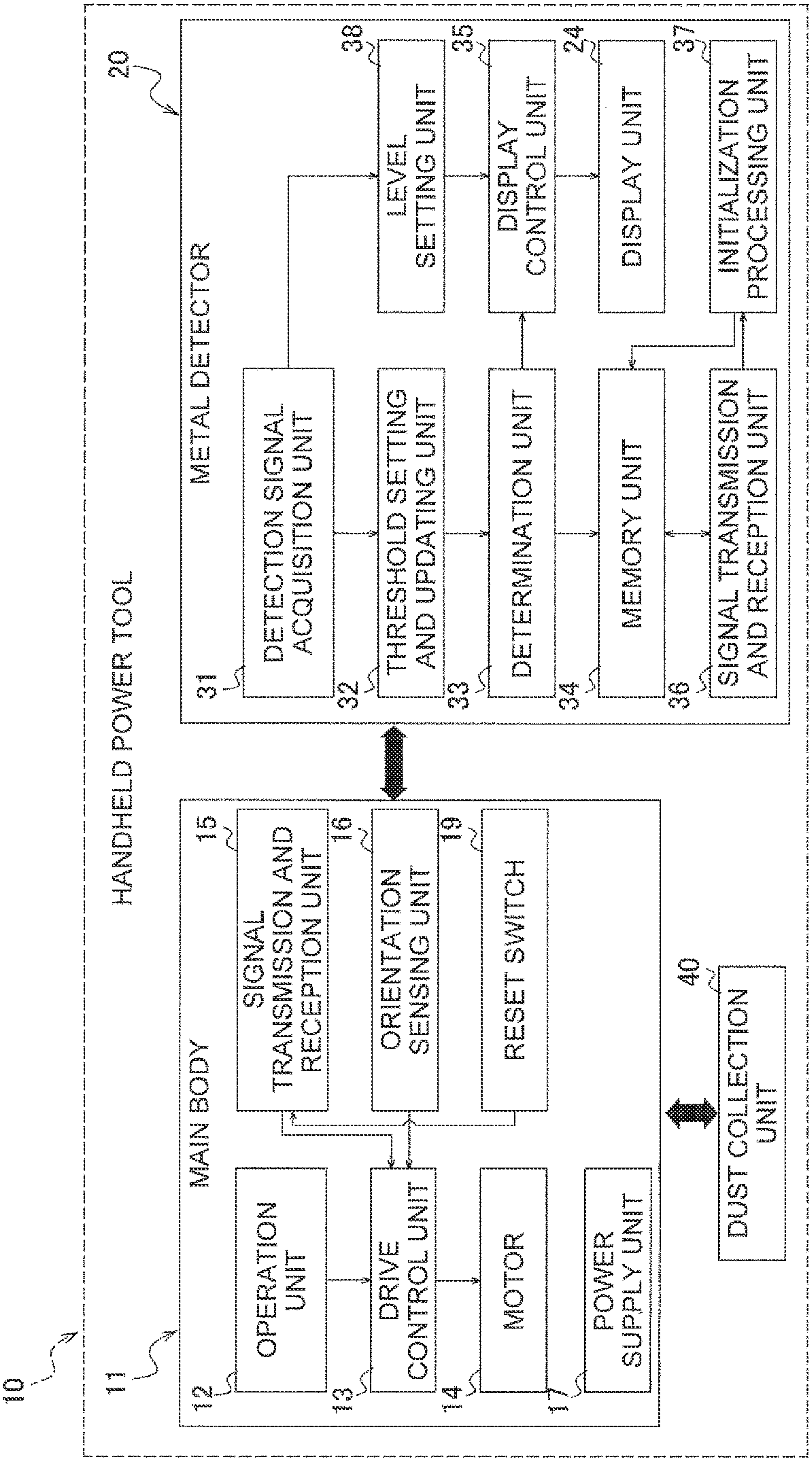
FIG. 8 is a control block diagram of the handheld power tool in FIG. 2, etc.

As shown in FIG. 8, the main body 11 has an operation unit 12, a drive control unit 13, a motor (drive unit) 14, a signal transmission and reception unit 15, an orientation sensing unit 16, a power supply unit 17, and a reset switch 19.

The operation unit 12 is connected to the trigger switch 12*a* of the handheld power tool 10, detects how much the trigger switch 12*a* has been operated, and transmits this amount to the drive control unit 13.

The drive control unit 13 controls the rotation speed of the motor 14 according to the operation amount of the trigger switch 12*a* received from the operation unit 12. Also, the drive control unit 13 receives a drive prohibition signal or a drive permission signal transmitted from the signal transmission and reception unit 36 according to the determination result by the determination unit 33 of the metal detector 20, and either prohibits or permits the drive of the motor 14.

The drive of the motor (drive unit) 14 is controlled by the drive control unit 13, and the tip portion 18 to which the tip tool 18*a* is mounted is rotationally driven to perform drilling or other such work on the surface of the concrete W.

The signal transmission and reception unit 15 can communicate with the signal transmission and reception unit 36 on the metal detector 20 side, receives the determination result or the like from the determination unit 33 of the metal detector 20, and transmits this result to the drive control unit 13. When the reset switch 19 provided on the main body 11 side is operated, or when the orientation sensing unit 16 senses that the handheld power tool 10 is in a predetermined orientation, the signal transmission and reception unit 15 sends an initialization signal for initializing the metal detector 20 to the metal detector 20 side.

The orientation sensing unit 16 is, for example, a gyro sensor provided for sensing that the handheld power tool 10 is in a predetermined orientation. The orientation sensing unit 16 senses, for example, that the handheld power tool 10 has moved from a lateral orientation to a vertical, upward-facing orientation.

With the handheld power tool 10 in this embodiment, the initialization process is automatically performed, for example, by sensing a specific orientation of the handheld power tool 10 in this way.

That is, the initialization processing for initializing the detection result from the metal detector 20, the set threshold value, etc., may be performed not only upon manual operation of the reset switch 19, but also when the orientation sensing unit 16 senses that the handheld power tool 10 is in a specific orientation.

Consequently, the operator does not have to manually press the reset switch 19 every time the place where metal is to be detected changes, for example, so the operator only needs to put the handheld power tool 10 in a specific orientation when initialization is to be performed, and the initialization processing can be automatically performed to detect the rebar W1 and perform work at a new location.

The power supply unit 17 supplies electric power from the above-mentioned rechargeable battery 17*a*, and also supplies power to the components inside the main body 11, to the components of the metal detector 20, and to the dust collecting unit 40.

The reset switch 19 is a manual switch that is provided at the base portion of the above-mentioned grip portion 11*a* and is pressed when the initialization processing of the metal detector 20 is performed. For example, this switch is operated by the thumb of the operator's left hand.

As shown in FIG. 8, the metal detector 20 has a detection signal acquisition unit 31, a threshold value setting and updating unit (threshold value setting unit, threshold value updating unit) 32, a determination unit 33, a memory unit 34, a display control unit 35, a display unit 24, a signal transmission and reception unit (prohibition signal transmission unit, permission signal transmission unit) 36, an initialization processing unit 37, and a level setting unit 38.

The detection signal acquisition unit 31 acquires a detection signal indicating a change in the impedance of the coil 22*b* sensed by the detector unit 22 in FIG. 6. The detection signal acquisition unit 31 then transmits the acquired detection signal to the threshold value setting and updating unit 32 and the level setting unit 38.

Figure 9:
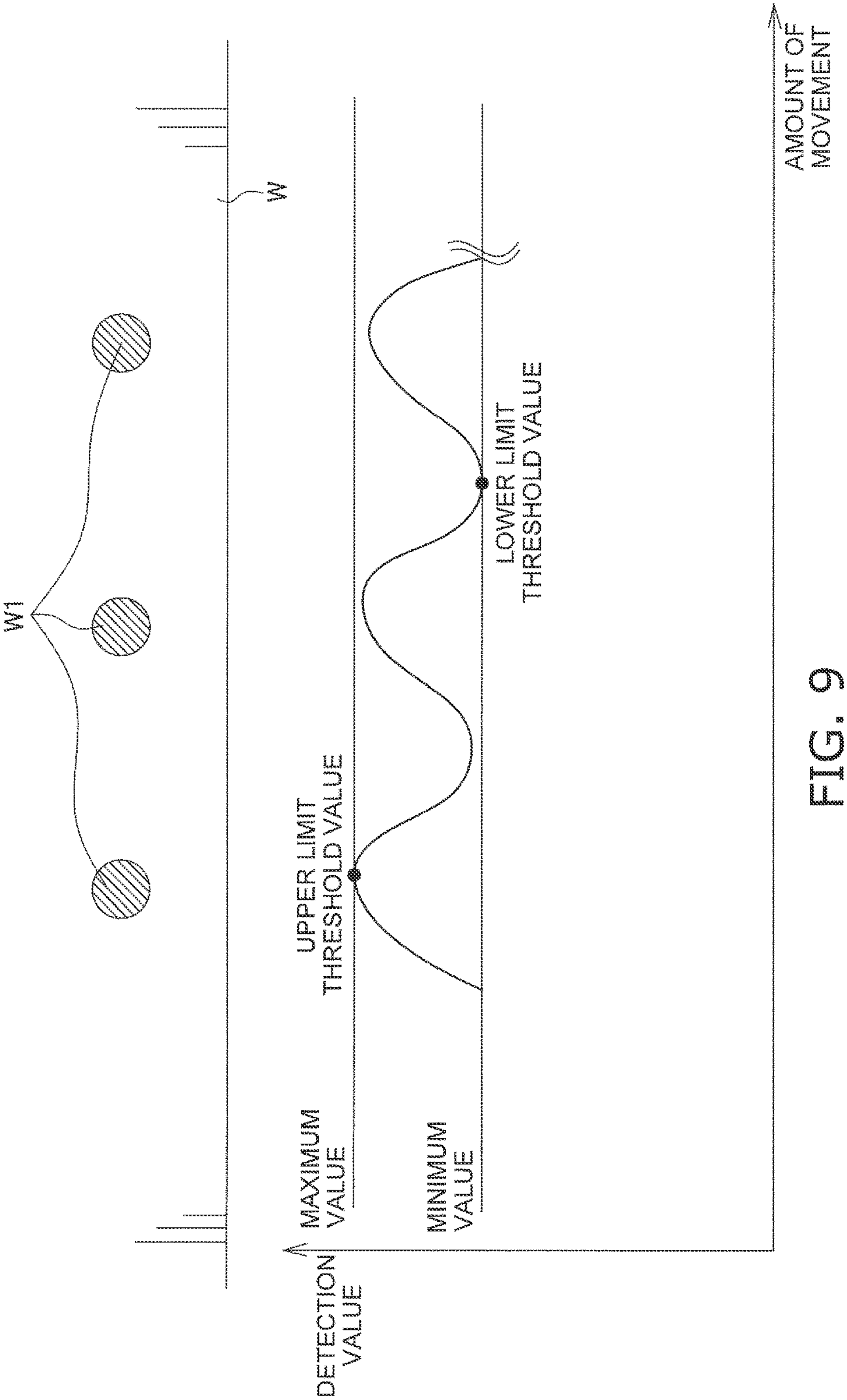
FIG. 9 is a diagram illustrating a metal detection method using the handheld power tool in FIG. 2, etc.

The threshold value setting and updating unit (threshold value setting unit, threshold value updating unit) 32 sets the maximum value and the minimum value of the detection signal, where were acquired by the detection signal acquisition unit 31 while the metal detector 20 was moved over the surface of the concrete W, as an upper limit threshold value and a lower limit threshold value for metal detection determination (see FIG. 9). The threshold value setting and updating unit 32 then updates the upper limit threshold value if the detection signal acquired by the detection signal acquisition unit 31 while the metal detector 20 was moved further over the surface of the concrete W is above the set upper limit threshold value, and updates the lower limit threshold value if this signal is below the set lower limit threshold value.

The updating of the upper limit threshold value and the lower limit threshold value by the threshold value setting and updating unit 32 is repeated if the result is higher than the set upper limit threshold value during one scanning with the metal detector 20, and if lower than the set lower limit threshold value.

Consequently, the rebar W1 can be detected more accurately by determining the presence or absence of the rebar W1 by using the latest upper limit threshold value and lower limit threshold value according to the detection signal acquired by the detection signal acquisition unit 31, The determination unit 33 determines the presence or absence of the rebar W1 or the approximate distance to the rebar W1 by using the upper limit threshold value and the lower limit threshold value set by the threshold value setting and updating unit 32, on the basis of the detection signal acquired by the detection signal acquisition unit 31.

More specifically, as shown in FIG. 9, when the metal detector 20 is scanned from left to right in the drawing in order to detect the position of the rebar W1 embedded in the concrete W, for example, the detection value goes up and down according to the change in the detection intensity from the rebar W1 along with the movement of the metal detector 20.

At this point, the determination unit 33 determines the presence or absence of the rebar W1 by using the determination-use upper limit threshold value and lower limit threshold value set by the above-mentioned threshold value setting and updating unit 32.

For example, FIG. 9 shows a composite detection graph in which a series of detection value peaks is produced by a plurality of rebars W1 embedded in the concrete W.

In the graph shown in FIG. 9, for example, it is determined that the rebar W1 is at the position where the detection value is at or above the upper limit threshold value. Also, in the graph shown in FIG. 9, it is determined that there is no rebar W1 in the vicinity of the position where the detection value is at or below the lower limit threshold value.

That is, in this embodiment, the determination unit 33 determines the presence or absence of the rebar W1 by comparing the upper limit threshold value and the lower limit threshold value with the detection signal while setting and updating the upper limit threshold value and the lower limit threshold value using the detection signal acquired by the detection signal acquisition unit 31 while the metal detector 20 is moved over the surface of the concrete W.

Also, in the graph shown in FIG. 9, the maximum value that first appears as a detection value is set as the upper limit threshold value, without being updated right away.

On the other hand, in the graph shown in FIG. 9, the minimum value that first appears as a detection value is updated because the minimum value that appears second is small, and the second-lowest value is set as the lower limit threshold value.

Consequently, the determination unit 33 can determine the presence or absence of metal by using the upper limit threshold value and the lower limit threshold value that have been newly set after the update, for example.

The memory unit 34 stores the detection signal acquired by the detection signal acquisition unit 31, the upper limit threshold value and the lower limit threshold value set and updated by the threshold value setting and updating unit 32, the determination result from the determination unit 33, and so forth.

The display control unit 35 controls the display unit 24 so as to change the lit color of the eight LEDs **24*b* included in the display unit 24, on the basis of the determination result made by the determination unit 33, which is performed using the upper limit threshold value and the lower limit threshold value set and updated by the threshold value setting and updating unit 32. Also, the display control unit 35 decides on the lit color of the eight LEDs 24*b* on the basis of the level table set in the level setting unit 38 (discussed below). For example, the display control unit 35 lights the eight LEDs 24*b* in green in the initial state or when it is determined that there is no rebar W1, and changes the lit color of one or more LEDs 24*b* in the order of green, yellow, and red, according to the level table set in the level setting unit 38** as the rebar W1 is approached.

Furthermore, when no rebar W1 is detected and the trigger switch **12*a* is in its ON state, the display control unit 35 lights the eight LEDs 24*b*** in white to illuminate and assist in the work being performed on the surface of the concrete W.

More precisely, in the graph shown in FIG. 9, the display control unit 35 gradually changes the lit color of the LEDs **24*b* of the display unit 24 on the basis of the determination result from the determination unit 33**, thereby notifying the operator that this is not a position where rebar W1 is present.

As described above, the signal transmission and reception unit 36 can communicate with the signal transmission and reception unit 15 on the main body 11 side of the handheld power tool 10, and transmits the determination result of the determination unit 33 of the metal detector 20, etc. Also, the signal transmission and reception unit 36 receives from the main body 11 side an initialization signal for the initialization processing of the metal detector 20 when the reset switch 19 provided on the main body 11 side is operated, or when the orientation sensing unit 16 senses a specific orientation.

The initialization processing unit 37 performs initialization processing to erase the detection result of the rebar W1 stored in the memory unit 34 as a result of sensing of the orientation of the handheld power tool 10 by the orientation sensing unit 16, or by operation of the reset switch 19.

The level setting unit 38 sets a level table in which the level between the maximum value and the minimum value of the detection signal received from the detection signal acquisition unit 31 is divided up into a plurality of levels. More specifically, assuming the maximum value to be 1500 and the minimum value to be 220, for example, the level setting unit 38 sets a level table consisting of 16 levels using the following relational expression (1), as shown in FIG. 10.

$$\text{Minimum value}+(\text{maximum value}-\text{minimum value})/16\times\text{number of levels} \quad (1)$$

That is, when level between the maximum value 1500 and the minimum value 220 is divided up into 16 parts, 17 levels are set, namely, 1500, 1420, 1340, 1260, 1180, 1100, 1020, 940, 860, 780, 700, 620, 540, 460, 380, 300, and 220, in decreasing order of the magnitude of the detection signal value (starting with the one closest to the rebar W1).

As shown in FIG. 10, the levels 0 to 16 set by the level setting unit 38 are such that level 0 is the level farthest from the rebar W1 (there is no rebar W1), and level 16 is the level closest to the rebar W1.

At level 0, as shown in FIG. 10, the display control unit 35 lights all eight LEDs **24*b*** in green.

At level 1, as shown in FIG. 10, the display control unit 35 lights seven of the LEDs **24*b* in green and one LED 24*b*** in yellow.

At level 2, as shown in FIG. 10, the display control unit 35 lights six of the LEDs **24*b* in green and two of the LEDs 24*b*** in yellow.

At level 3, as shown in FIG. 10, the display control unit 35 lights five of the LEDs **24*b* in green and three of the LEDs 24*b*** in yellow.

At level 4, as shown in FIG. 10, the display control unit 35 lights four of the LEDs **24*b* in green and four of the LEDs 24*b*** in yellow.

At level 5, as shown in FIG. 10, the display control unit 35 lights three of the LEDs **24*b* in green and five of the LEDs 24*b*** in yellow.

At level 6, as shown in FIG. 10, the display control unit 35 lights two of the LEDs **24*b* in green and six of the LEDs 24*b*** in yellow.

At level 7, as shown in FIG. 10, the display control unit 35 lights one of the LEDs **24*b* in green and seven of the LEDs 24*b*** in yellow.

At level 8, as shown in FIG. 10, the display control unit 35 lights all eight LEDs **24*b*** in yellow.

At level 9, as shown in FIG. 10, the display control unit 35 lights seven of the LEDs **24*b* in yellow and one of the LEDs 24*b*** in red.

At level 10, as shown in FIG. 10, the display control unit 35 lights six of the LEDs 24*b* in yellow and two of the LEDs 24*b* in red.

At level 11, as shown in FIG. 10, the display control unit 35 lights five of the LEDs 24*b* in yellow and three of the LEDs 24*b* in red.

At level 12, as shown in FIG. 10, the display control unit 35 lights four of the LEDs 24*b* in yellow and four of the LEDs 24*b* in red.

At level 13, as shown in FIG. 10, the display control unit 35 lights three of the LEDs 24*b* in yellow and five of the LEDs 24*b* in red.

At level 14, as shown in FIG. 10, the display control unit 35 lights two of the LEDs 24*b* in yellow and six of the LEDs 24*b* in red.

At level 15, as shown in FIG. 10, the display control unit 35 lights one of the LEDs 24*b* in yellow and seven of the LEDs 24*b* in red.

At level 16, as shown in FIG. 10, the display control unit 35 lights all eight LEDs 24*b* in red.

Consequently, the display control unit 35 can set the lighting color of the eight LEDs 24*b* of the display unit 24 by referring to which of the 17 levels, from level 0 to level 16, set by the level setting unit 38 corresponds to the value of the detection signal acquired by the detection signal acquisition unit 31.

Next, FIGS. 11A to 13D show the control for switching the lighting color of the LEDs 24*b* of the display unit 24 according to the determination result of the determination unit 33 and the level table set in the level setting unit 38.

Figures 11A, 11B, 11C, 11D, 11E, 11F:
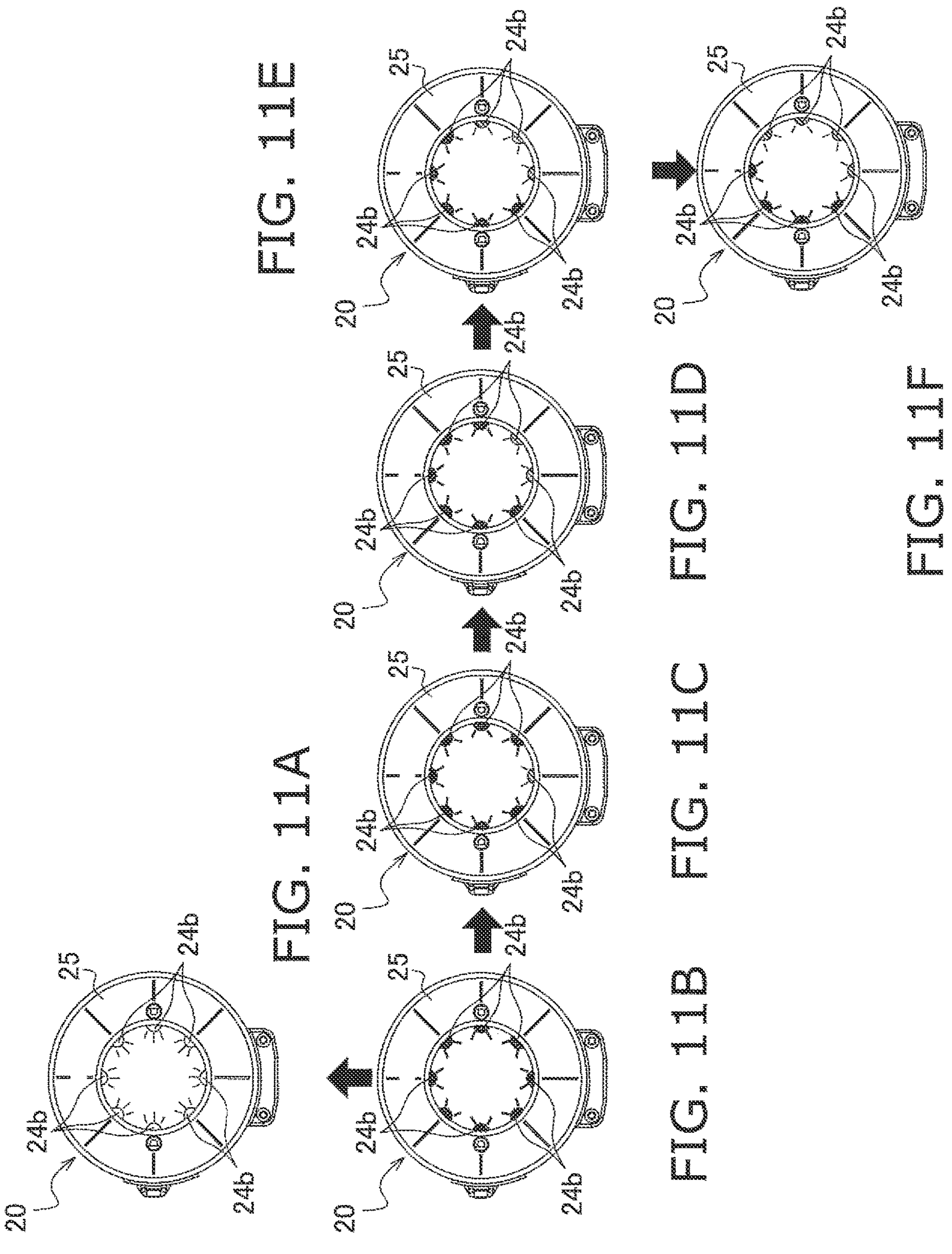
FIGS. 11A to 11F are diagrams showing control for displaying different colors of light on the display unit of the metal detector in FIG. 6 according to the determination result indicating the presence or absence of metal.

That is, FIG. 11B shows the display in the initial state or when there is no rebar W1 nearby, and shows the state in which all eight of the LEDs 24*b* of the display unit 24 are lit in green light (level 0).

FIG. 11A shows a state in which the above-mentioned white light used during work is turned on from the initial state, etc., in FIG. 11B.

From the initial state in FIG. 11B up to FIGS. 11C through 11E, the lighting color of from one to three of the eight LEDs 24*b* is changed from green to yellow (levels 1 to 3) in order to notify the operator that this is an area where drilling or the like is possible, although it is drawing closer to the rebar W1.

More specifically, in the lighting state shown in FIG. 11C (level 1) the one at the very bottom is yellow while the others are green, in the lighting state shown in FIG. 11D (level 2) the very bottom and the one to the right are yellow while the others are green, and in the lighting state shown in FIG. 11E (level 3), the very bottom and the two to the right are yellow while the others are green.

The operator can preset the lit areas shown in FIGS. 11B to 11E as areas in which drilling or other such work can be performed.

Next, FIG. 11F shows the state in which the rebar W1 is now closer and the lighting color of four of the eight LEDs 24*b* has changed from green to yellow (the very bottom and the three to the right are yellow while the others are green) (level 4).

Consequently, the operator can set the lit area shown in FIG. 11F as an area where work is not possible.

Similarly, FIGS. 12A to 12D show the state in which the rebar W1 is now even closer, and the lighting color ranges from when five of the eight LEDs 24*b* are yellow (the five from the very bottom to the very top are yellow while the rest are green) (level 5), to when all eight of the LEDs 24*b* are yellow (level 8).

Consequently, the operator can similarly set the lit areas shown in FIGS. 12A to 12D as areas in which work is not possible.

As the rebar W1 approaches even nearer, as shown in FIGS. 12E to 12H, the lighting color of from one to three of the eight LEDs 24*b* changes from yellow to red.

Figures 12A, 12B, 12C, 12D, 12E, 12F, 12G, 12H:
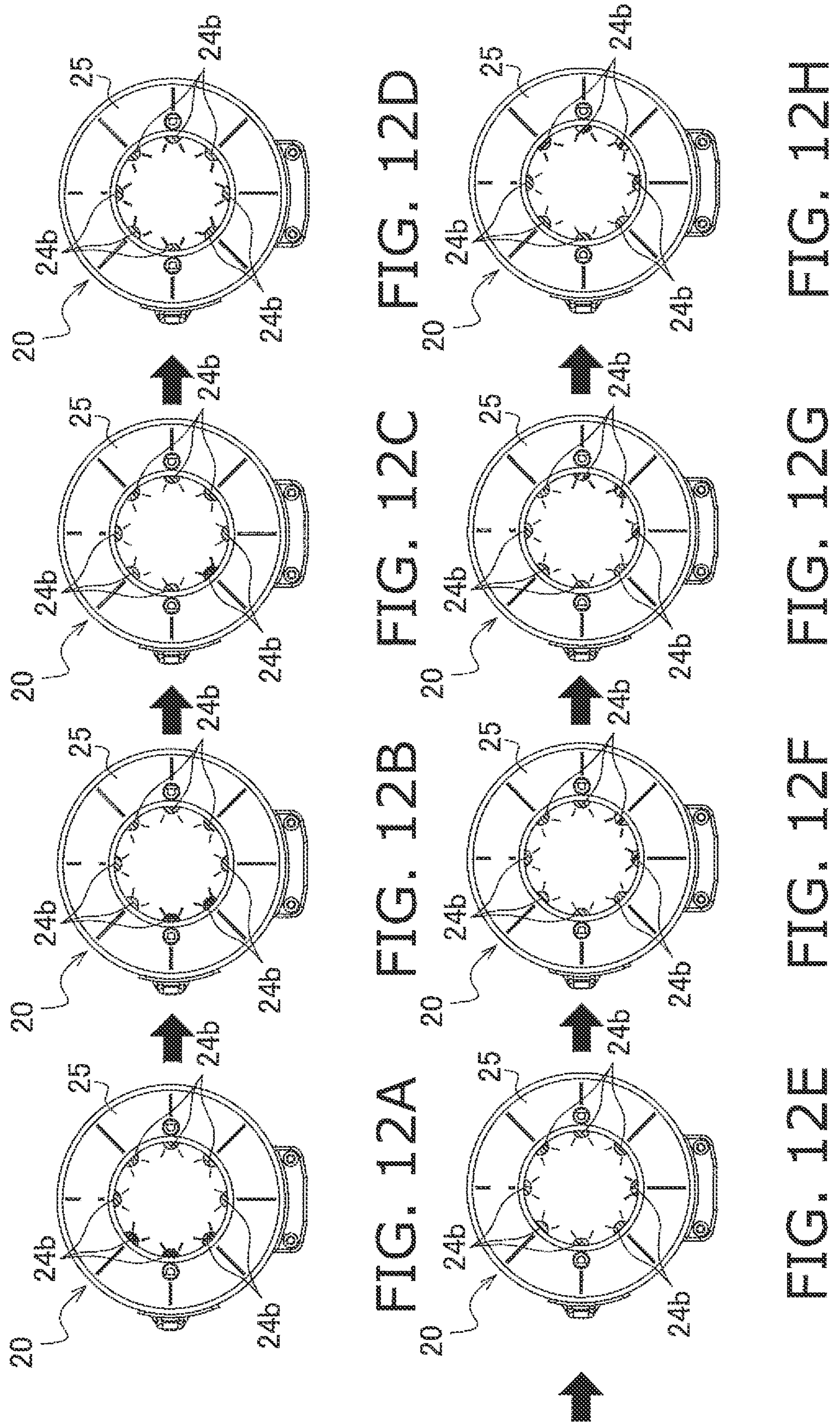
FIGS. 12A to 12H are diagrams showing control for displaying different colors of light on the display unit of the metal detector in FIG. 6 according to the determination result indicating the presence or absence of metal.
Figures 13A, 13B, 13C, 13D:
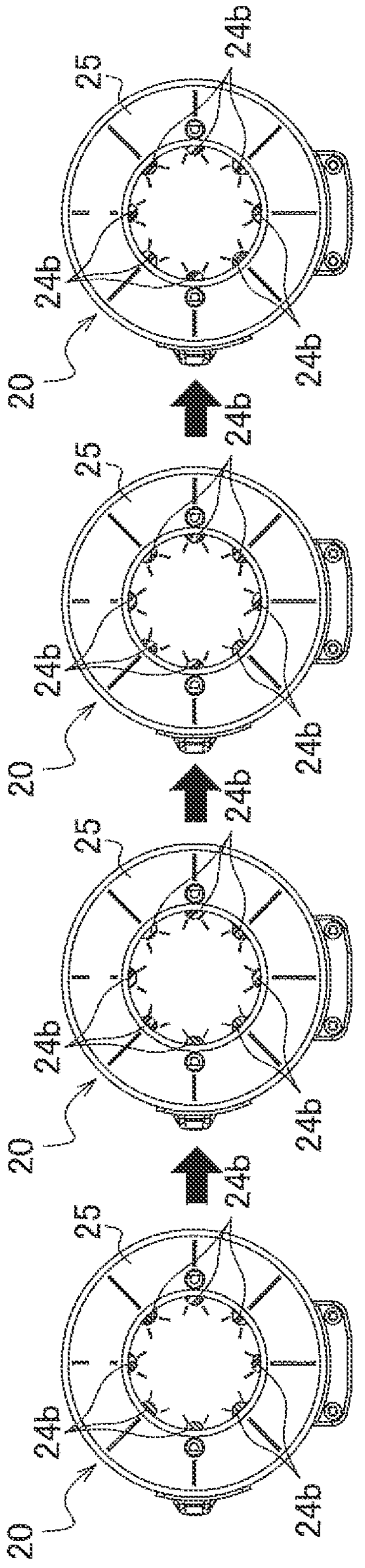
FIGS. 13A to 13D are diagrams showing control for displaying different colors of light on the display unit of the metal detector in FIG. 6 according to the determination result indicating the presence or absence of metal.

More specifically, in the lighting state shown in FIG. 12E (level 9), the one at the very bottom is red while the others are yellow, in the lighting state shown in FIG. 12F (level 10), the one at the very bottom and the one to the right are red while the others are yellow, in the lighting state shown in FIG. 12G (level 11), the one at the very bottom and the two to the right are red while the others are yellow, and in the lighting state shown in FIG. 12H (level 12), the one at the very bottom and the three to the right are red while the others are yellow.

The operator can preset the areas in the lighting state shown in FIGS. 12E to 12H (levels 9 to 12) as area where drilling or other such work is not possible.

As the rebar W1 approaches even nearer from here, as shown in FIGS. 13A to 13D, the lighting color of from five to all eight of the LEDs 24*b* changes from yellow to red.

Consequently, the operator can set the areas in the lighting states shown in FIGS. 13A to 13D (levels 13 to 16) as areas in which the distance from the rebar W1 is particularly short and work is therefore not possible.

With the handheld power tool 10 in this embodiment, the operator can check the lighting color displayed on the display unit 24, which changes on the basis of the detection result for the rebar W1 in the metal detector 20, and can designate areas where drilling or other such work is possible (areas without rebar W1) on the basis of the detection result. This means that the operator can safely carry out the work while preventing the tip tool 18*a* from coming into contact with rebar W1 during the work.

Metal Detection Method Using the Metal Detector 20

With a metal detection method that makes use of the metal detector 20 in this embodiment, processing is performed according to the flowcharts shown in FIGS. 14 to 19, by the components described above.

Figure 14:
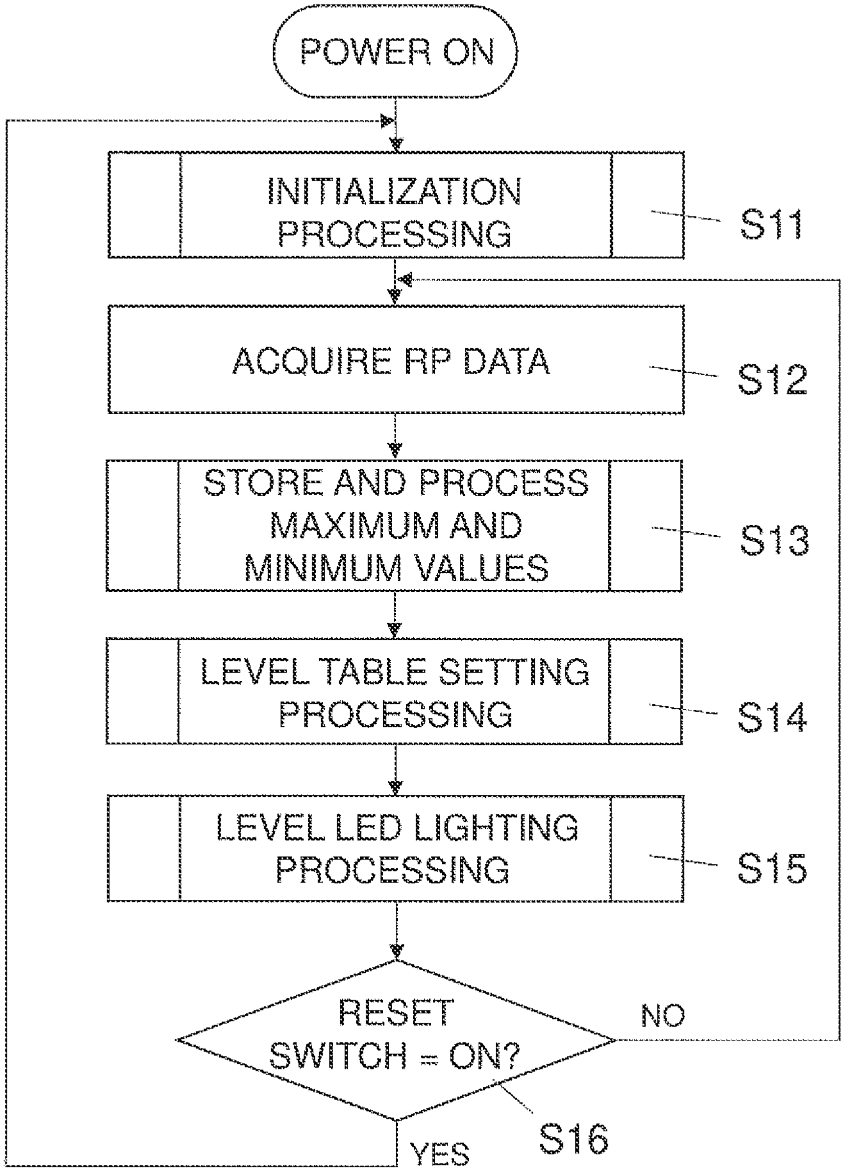
FIG. 14 is a main flowchart showing the flow of processing in a metal detection method using the metal detector in FIG. 6.

FIG. 14 shows the main flow, including initialization processing, level table setting processing, and level LED lighting processing performed in the metal detector 20.

That is, in step S11, when the power is turned on or the reset switch 19 is pressed, for example, initialization processing is performed by the initialization processing unit 37 of the metal detector 20 described above. More specifically, the initialization processing unit 37 performs initialization processing to erase the detection signal, upper limit threshold value, lower limit threshold value, determination result, and the like stored in the memory unit 34 of the metal detector 20.

At this point, the display control unit 35 lights the eight LEDs 24*b* of the display unit 24 in green to indicate the initial state (level 0) shown in FIG. 11B.

Next, in step S12, the above-mentioned detection signal acquisition unit 31 of the metal detector 20 acquires Rp data (detection signal).

Next, in step S13, the threshold value setting and updating unit 32 of the metal detector 20 detects the maximum value and the minimum value of the Rp data acquired in step S12, and stores these in the memory unit 34.

Next, in step S14, the level setting unit 38 of the metal detector 20 performs level table setting processing by using the maximum value and the minimum value of the Rp data acquired in step S12.

Next, in step S15, the display control unit 35 of the metal detector 20 performs level LED lighting processing to control the lighting colors of the eight LEDs 24*b* of the display unit 24 on the basis of the level table set in step S14.

Next, in step S16, it is determined whether or not the reset switch 19 has been operated to be in the ON state, and if it is ON, the processing goes back to step S11 and the initialization processing is performed again to determine metal detection at another location, for example.

On the other hand, if the reset switch 19 is not in its ON state, the processing goes back to step S12, and the determination of metal detection at the same location, for example, is continuously performed without performing the initialization processing.

Figure 15:
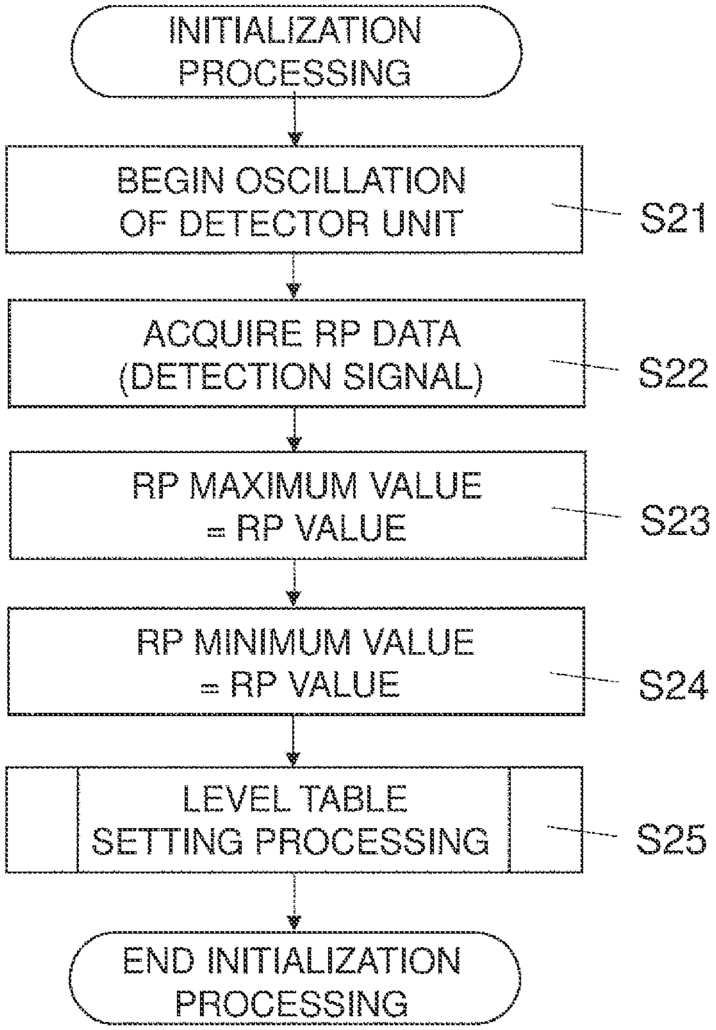
FIG. 15 is a flowchart showing the detailed flow of the initialization processing in FIG. 14.

FIG. 15 shows the detailed flow of processing in the initialization processing of step S11 in FIG. 14.

That is, in step S21, the coil 22*b* of the detector unit 22 begins oscillating in order to acquire a detection signal for the rebar W1 in a state in which the metal detector 20 is in contact with the surface of the concrete W where the rebar W1 is to be detected.

Next, in step S22, the detection signal acquisition unit 31 of the metal detector 20 acquires Rp data (detection signal) indicating the degree to which the rebar W1 has been detected.

Next, in steps S23 and S24, the maximum value and the minimum value in the detection signal acquired by the detection signal acquisition unit 31 are set as the Rp maximum value and the Rp minimum value, respectively.

Next, in step S25, the level setting unit 38 divides up the level between the maximum value and the minimum value set in steps S23 and S24 into 16 levels, performs level table setting processing to switch the lighting color of the LEDs 24*b* of the display unit 24, and ends the initialization processing.

Figure 16:
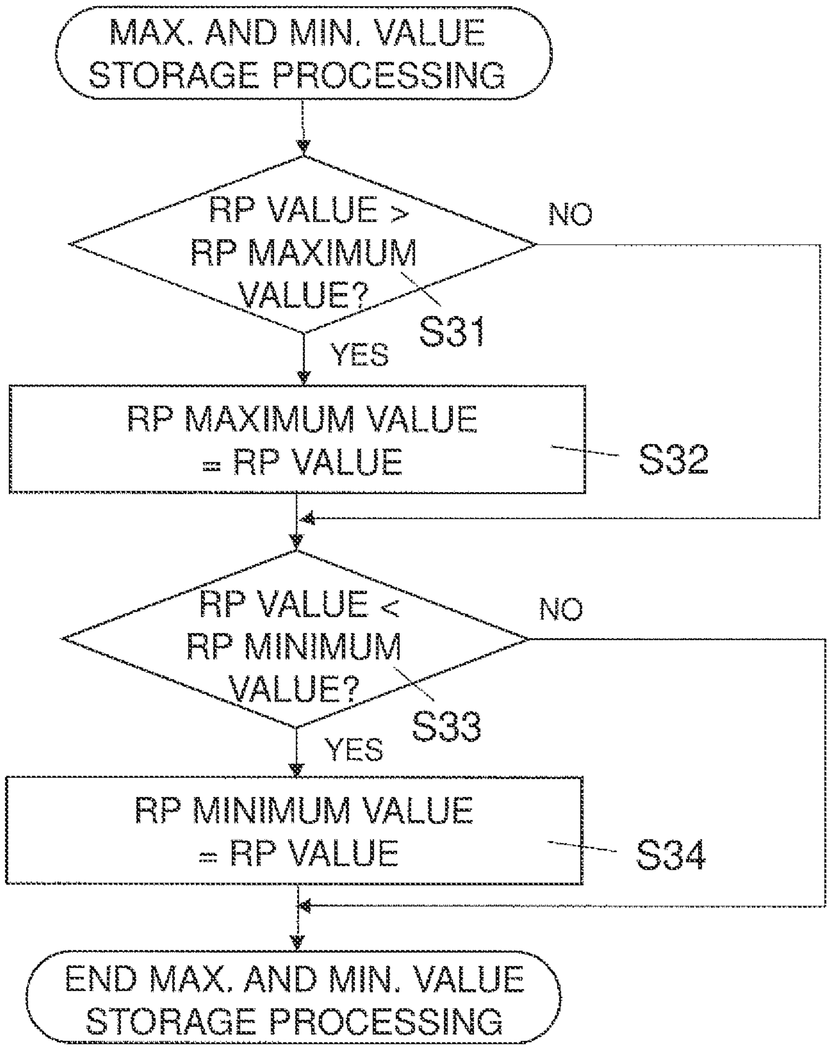
FIG. 16 is a flowchart showing the detailed flow of the maximum value and minimum value save processing in FIG. 14.

FIG. 16 shows the detailed flow of processing in the maximum value and minimum value saving processing in step S13 of FIG. 14.

That is, in step S31, the acquired detection signal value (Rp value) is compared with the Rp maximum value set in step S23. Here, if the Rp value of the acquired detection signal is larger than the maximum Rp value, the processing proceeds to step S32, and if it is equal to or less than the maximum Rp value, the processing proceeds to step S33.

Next, in step S32, since it was determined in step S31 that the Rp value was larger than the maximum Rp value, the newly acquired Rp value of the detection signal is stored in the memory unit 34 as the maximum value.

Next, in step S33, the acquired detection signal value (Rp value) is compared with the Rp minimum value set in step S24. Here, if the Rp value of the acquired detection signal is smaller than the Rp minimum value, the processing proceeds to step S34, and if it is equal to or greater than the Rp minimum value, the processing is ended.

Next, in step S34, since it was determined in step S33 that the Rp value was smaller than the Rp minimum value, the newly acquired Rp value of the detection signal is stored in the memory unit 34 as the minimum value, and the processing is ended.

Figure 17:
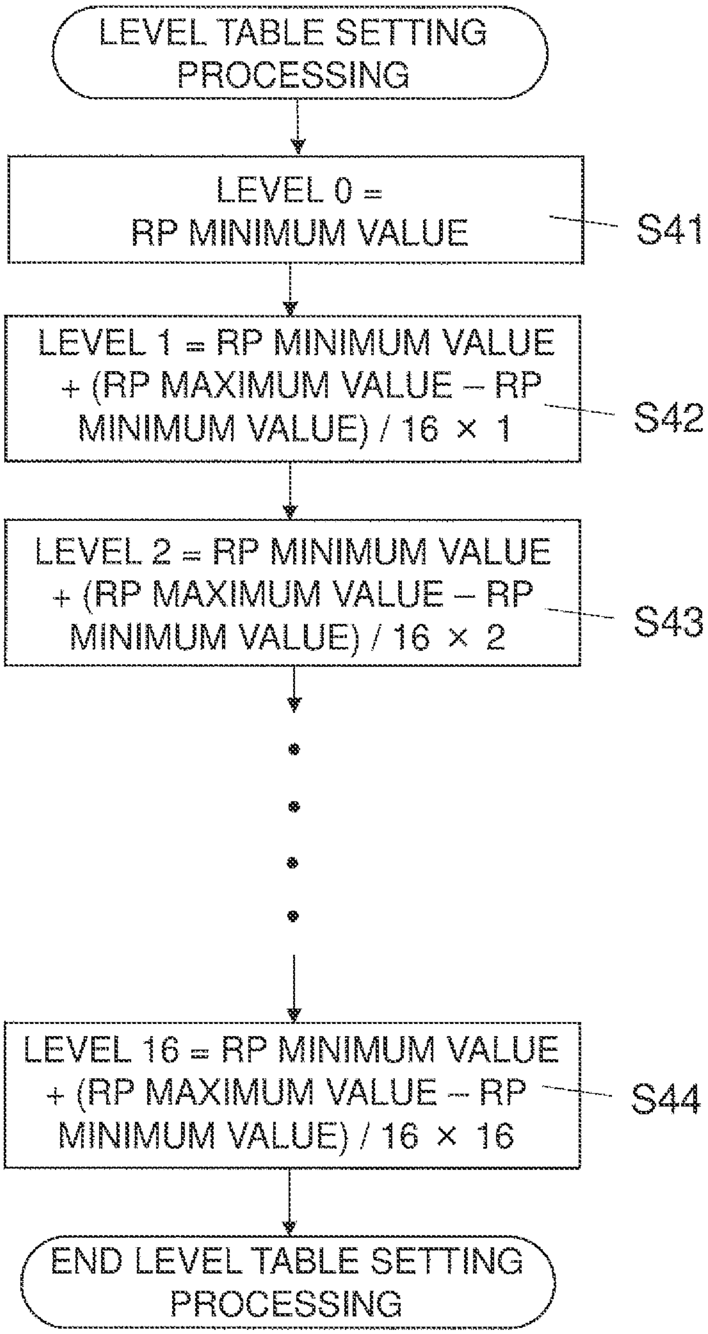
FIG. 17 is a flowchart showing the detailed flow of the level table setting processing in FIG. 14.

FIG. 17 shows the detailed flow of processing in the level table setting processing in step S14 of FIG. 14.

That is, in the level table setting processing shown in FIG. 17, the level setting unit 38 of the metal detector 20 sets a level table (see FIG. 10) that decides the lighting color of the eight LEDs 24*b* of the display unit 24 by using the Rp maximum value and the Rp minimum value stored in the memory unit 34 in the maximum value and minimum value storage processing shown in FIG. 16.

More specifically, the level setting unit 38 uses the above-mentioned relational expression (1) to set levels 0 to 16 between the Rp maximum value and the Rp minimum value stored in the memory unit 34.

In step S41, the level setting unit 38 sets the Rp minimum value as level 0.

Next, in step S42, the level setting unit 38 uses the above-mentioned relational expression (1) to set level 1.

Next, in step S43, the level setting unit 38 uses the above-mentioned relational expression (1) to set level 2.

Thereafter, the level setting unit 38 similarly sets levels 3 to 15 using the above-mentioned relational expression (1).

Next, in step S44, the level setting unit 38 sets level 16 and ends the processing.

Figure 18:
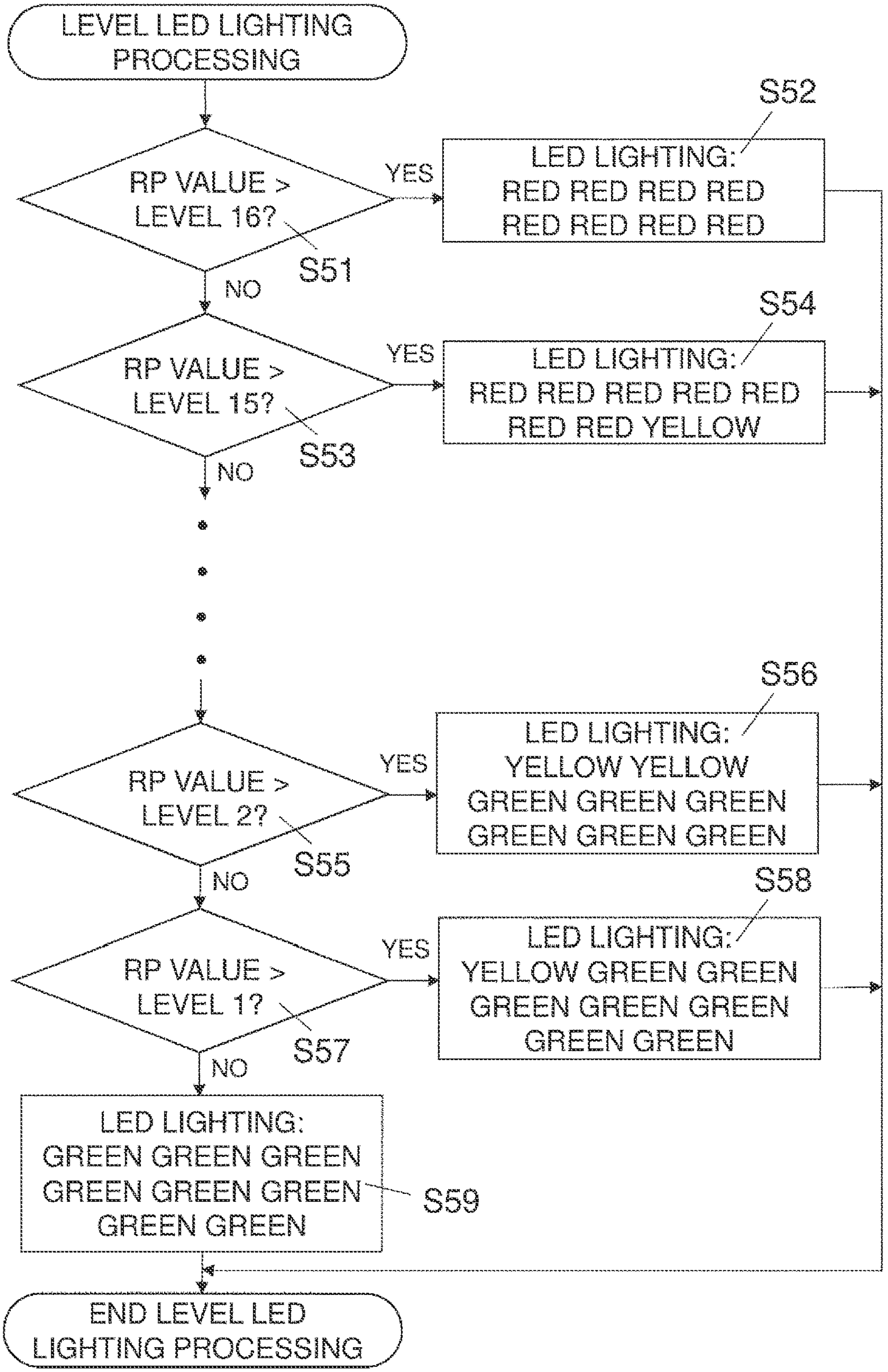
FIG. 18 is a flowchart showing the detailed flow of the level LED lighting processing in FIG. 14.

FIG. 18 shows the detailed flow of processing in the level LED lighting processing in step S15 of FIG. 14.

That is, in the level LED lighting processing shown in FIG. 18, the display control unit 35 sets the lighting colors of the eight LEDs 24*b* of the display unit 24 on the basis of the 16-step level table set by the level setting unit 38.

In step S51, the determination unit 33 determines whether or not the Rp value of the detection signal acquired by the detection signal acquisition unit 31 of the metal detector 20 is larger than the value 1500 corresponding to level 16 (see FIG. 10).

Here, if the acquired Rp value is larger than the value 1500 corresponding to level 16, the processing proceeds to step S52, and if it is 1500 or less, the processing proceeds to step S53.

In step S52, since it was determined in step S51 that the acquired Rp value was larger than the value 1500 corresponding to level 16, the display control unit 35 controls the lighting such that all eight of the LEDs 24*b* of the display unit 24 are lit in red (as the lighting color corresponding to level 16), and the processing is ended.

Next, in step S53, since the acquired Rp value was determined in step S51 to be 1500 or less (corresponding to level 16), the determination unit 33 determines whether or not the Rp value of the acquired detection signal is a value of 1420 corresponding to level 15 (see FIG. 10).

Here, if the acquired Rp value is larger than the value 1420 corresponding to level 15, the processing proceeds to step S54, and if it is 1420 or less, the processing proceeds to step S55.

In step S54, since it was determined in step S53 that the acquired Rp value was larger than the value 1420 corresponding to level 15, the display control unit 35 performs lighting color so that one of the eight LEDs 24*b* of the display unit 24 is lit in yellow and the other seven are lit in red, and ends the processing.

Thereafter, similarly, the display control unit 35 determines whether or not the Rp value of the acquired detection signal is larger than the values 1340 to 460 corresponding to levels 14 to 3, and if it is larger than the value corresponding to each level, the lighting of the eight LEDs 24*b* of the display unit 24 is controlled, and the processing is ended.

On the other hand, if the Rp value of the acquired detection signal is equal to or less than the value corresponding to each level, it is determined whether or not this Rp value is larger than the value corresponding to each level, in the order of level 14, level 13, level 12, . . . , level 3.

Next, in step S55, the determination unit 33 determines whether or not the Rp value of the acquired detection signal is larger than the value 380 corresponding to level 2 (see FIG. 10).

Here, if the acquired Rp value is larger than a value of 380 (corresponding to level 2), the processing proceeds to step S56, and if it is 380 or less, the processing proceeds to step S57.

In step S56, since it was determined in step S55 that the acquired Rp value was larger than the value 380 corresponding to level 2, the display control unit 35 controls the lighting so that two of the eight LEDs 24*b* of the display unit 24 are lit in yellow and the other six are lit in green, and ends the processing.

Next, in step S57, since the acquired Rp value was determined in step S55 to be 380 or less (corresponding to level 2), the determination unit 33 determines whether or not the Rp value of the acquired detection signal is a value of 300 (corresponding to level 1) (see FIG. 10).

Here, if the acquired Rp value is larger than the value of 300 corresponding to level 1, the processing proceeds to step S58, and if it is 300 or less, the processing proceeds to step S59.

In step S58, since it was determined in step S57 that the acquired Rp value was larger than the value of 300 corresponding to level 1, the display control unit 35 controls the lighting so that one of the eight LEDs 24*b* of the display unit 24 is lit in yellow and the other seven are lit in green, and ends the processing.

Next, in step S59, since the acquired Rp value was determined in step S57 to be 300 or less (corresponding to level 1), the determination unit 33 determines that the acquired Rp value is level 0, and the display control unit 35 controls the lighting so that all eight of the LEDs 24*b* of the display unit 24 are lit green, and ends the processing.

Operation of Handheld Power Tool 10

Figure 19:
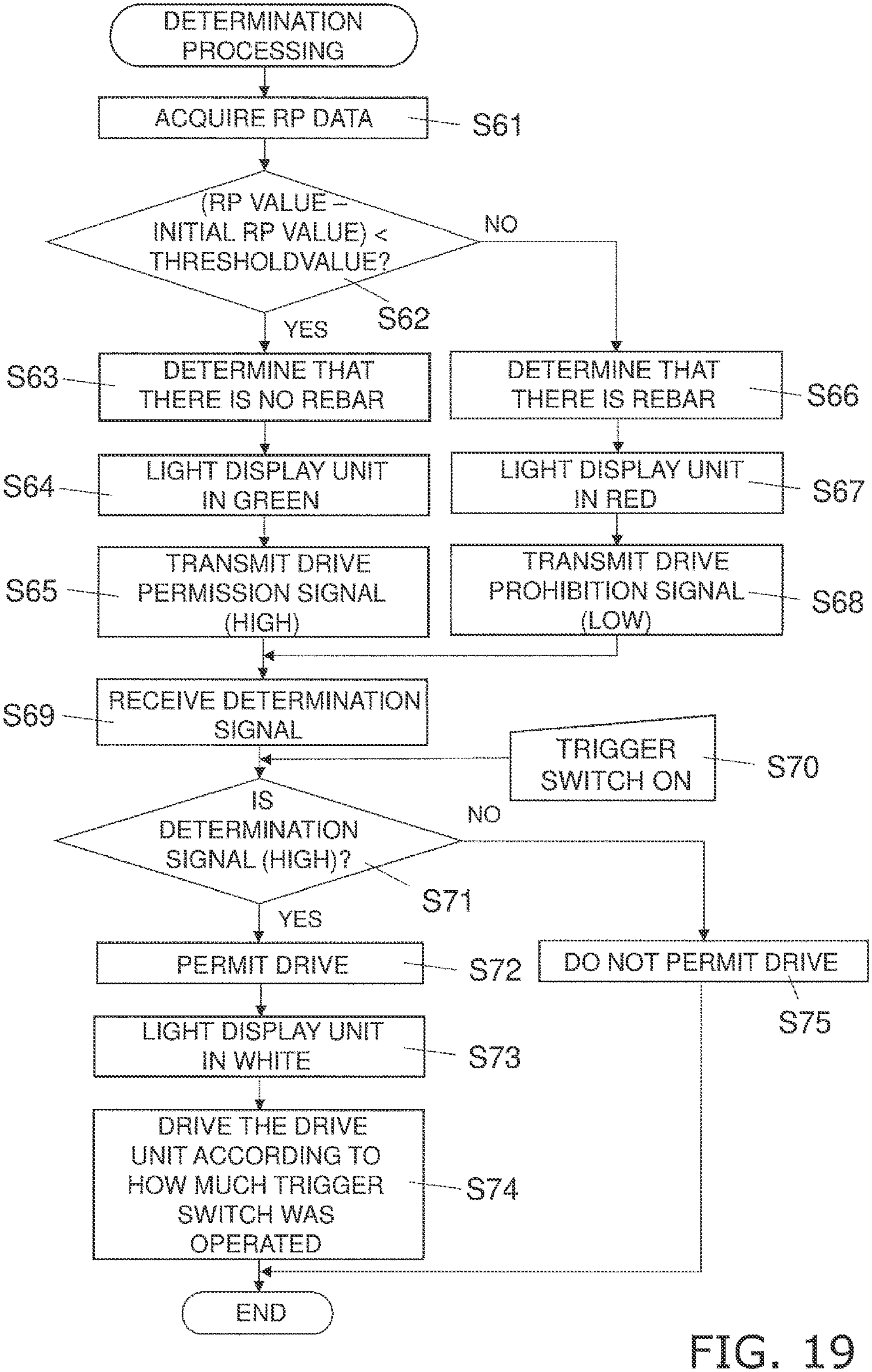
FIG. 19 is a flowchart showing the flow of operation of the handheld power tool in FIG. 1.

FIG. 19 is a flowchart showing the operational flow of the handheld power tool 10 after the above-mentioned metal detection method has been carried out with the metal detector 20.

That is, in step S61, in order to commence the detection of the rebar W1, the coil 22*b* of the detector unit 22 begins to oscillate in a state in which the metal detector 20 is in contact with the surface of the concrete W where the rebar W1 is to be detected, and the detection signal acquisition unit 31 acquires Rp data from the detector unit 22.

Next, in step S62, it is determined whether or not the difference (Rp value−initial Rp value) between the Rp value of the Rp data acquired in step S61 and the initial Rp value stored in the memory unit 34 is smaller than a specific threshold value.

If this difference is smaller than the threshold value, the processing proceeds to step S63, but if the difference is greater than or equal to the threshold value, the processing proceeds to step S66.

Next, in step S63, since it was determined in step S62 that (Rp value−initial Rp value)<threshold value, the determination unit 33 determines that there is no rebar W1.

Next, in step S64, since it was determined in step S63 that there was no rebar W1, that area is determined to be an area in which drive is permitted, and the LEDs 24*b* of the display unit 24 are lit in green.

Next, in step S65, based on the determination result from the determination unit 33 of the metal detector 20, the signal transmission and reception unit 36 sends the main body 11 a drive permission signal (High) for permitting the drive of the motor 14 of the main body 11.

On the other hand, in step S66, since it was determined in step S62 that (Rp value−initial Rp value)<threshold value, the determination unit 33 determines that rebar W1 is present.

Next, in step S67, since it was determined in step S66 that there was rebar W1, that area is determined to be an area in which drive is prohibited, and the LEDs 24*b* of the display unit 24 are lit in red.

Regarding the green lighting control in step S64 and the red lighting control in step S67, the lights may be lit to yellow in between the green light and the red light according to the distance to the rebar W1 (the magnitude of the Rp value).

Next, in step S68, based on the determination result from the determination unit 33 of the metal detector 20, the signal transmission and reception unit 36 sends the main body 11 a drive prohibition signal (Low) for prohibiting the driving of the motor 14 of the main body 11.

Next, in step S69, the signal transmission and reception unit 15 on the main body 11 side receives a determination signal (drive permission signal (High) or drive prohibition signal (Low)) from the signal transmission and reception unit 36 on the metal detector 20 side.

Next, in step S70, when the trigger switch 12*a* is operated to the ON position, it is determined in step S71 whether or not the received determination signal is a drive permission signal (High).

Here, if the determination signal received by the signal transmission and reception unit 15 is a drive permission signal (High), the processing proceeds to step S72. On the other hand, if the received determination signal is a drive prohibition signal (Low), the processing proceeds to step S75.

Next, in step S72, since the determination signal received by the signal transmission and reception unit 15 was determined in step S71 to be a drive permission signal (High), the drive control unit 13 permits drive of the motor 14.

Next, in step S73, the signal transmission and reception unit 36 transmits a drive permission signal, and in step S76, the trigger switch 12*a* is operated to the ON position, so the display control unit 35 lights the LEDs 24*b* of the display unit 24 in white.

Next, in step S74, the drive control unit 13 controls the rotation speed of the motor 14 according to how much the trigger switch 12*a* has been operated, to rotationally drive the tip tool 18*a*.

Consequently, the operator can carry out the work in a state in which the worksite portion is brightly illuminated by white light when the concrete W is being worked while avoiding the rebar W1.

As a result, the work is easier and safer for the operator.

On the other hand, in step S75, since it was determined in step S71 that the determination signal received by the signal transmission and reception unit 15 was not a drive permission signal (High), the signal transmission and reception unit 15 is determined to have received a drive prohibition signal (Low), the drive of the motor 14 is not permitted, and the processing is ended.

Consequently, the drive control unit 13 on the main body 11 side prohibits the drive of the motor 14 on the basis of the drive prohibition signal received by the signal transmission and reception unit 15.

Therefore, the drive control unit 13 can control not to drive the motor 14 by prohibiting the drive of the motor 14 on the main body 11 side, even if the trigger switch 12*a* is operated to the ON position in a drive prohibition area, when it has been determined that rebar W1 is near in a drive prohibition area.

As a result, the tip tool 18*a* can be prevented from coming into contact with the rebar W1 due to accidental work in a drive prohibition area near rebar W1.

Also, with the handheld power tool 10 in this embodiment, since the metal detector 20 is provided on the distal end side, the concrete W can be worked while avoiding the rebar W1 and while performing the processing to detect the rebar W1.

This means that there is no need to perform work such as marking the surface of the concrete W, as opposed to when rebar is detected using a conventional metal detector provided separately from the handheld power tool.

As a result, the work from the detection of the rebar W1 to the working of the concrete W will be easier than in a conventional case.

Furthermore, since the metal detector 20 notifies the operator of whether or not there is rebar W1 nearby by controlling the lighting of the LEDs 24*b* of the display unit 24, the metal detector 20 is easier to use in a noisy work environment than a conventional metal detector that notifies the operator with a warning sound.

Also, since the metal detector 20 is mounted in an integrated state on the distal end side of the handheld power tool 10, the work can be carried out continuously, from the detection of the rebar W1 to the working of the surface.

Furthermore, in this embodiment, if the metal detector 20 determines that rebar W1 is near, the color, number, etc., in which the lights are lit and displayed on the LEDs 24*b* of the display unit 24 are changes in stepwise fashion according to the distance to the rebar W1.

Consequently, on the surface of the concrete W, for example, the level can be set stepwise from the drive permission area to the drive prohibition area.

Here, the LEDs 24*b* showing the determination result for the presence or absence of rebar W1 in the metal detector 20 are disposed so as to face the inside diameter side of the substantially annular metal detector 20 (the tip tool 18*a* side of the handheld power tool 10).

This reduces the burden on the operator's eyes due to direct viewing of the light source, and because white light can be turned on during work using the handheld power tool 10, the place where the operator is working can be brightly illuminated to ensure better visibility.

The metal detector 20 can also be used alone, and the drilling work using the handheld power tool 10 and metal detection using the metal detector 20 can be performed in parallel.

Embodiment 2

A handheld power tool 100 according to another embodiment of the present invention will now be described with reference to FIGS. 20 to 23.

The handheld power tool 100 in this embodiment differs from Embodiment 1 above in that the dust collecting unit 40 is not attached to the main body 11, and the metal detector 20 is attached via a holder 101. In this embodiment, those components that are the same components as in the first embodiment are numbered the same and will not be described again.

Figure 20:
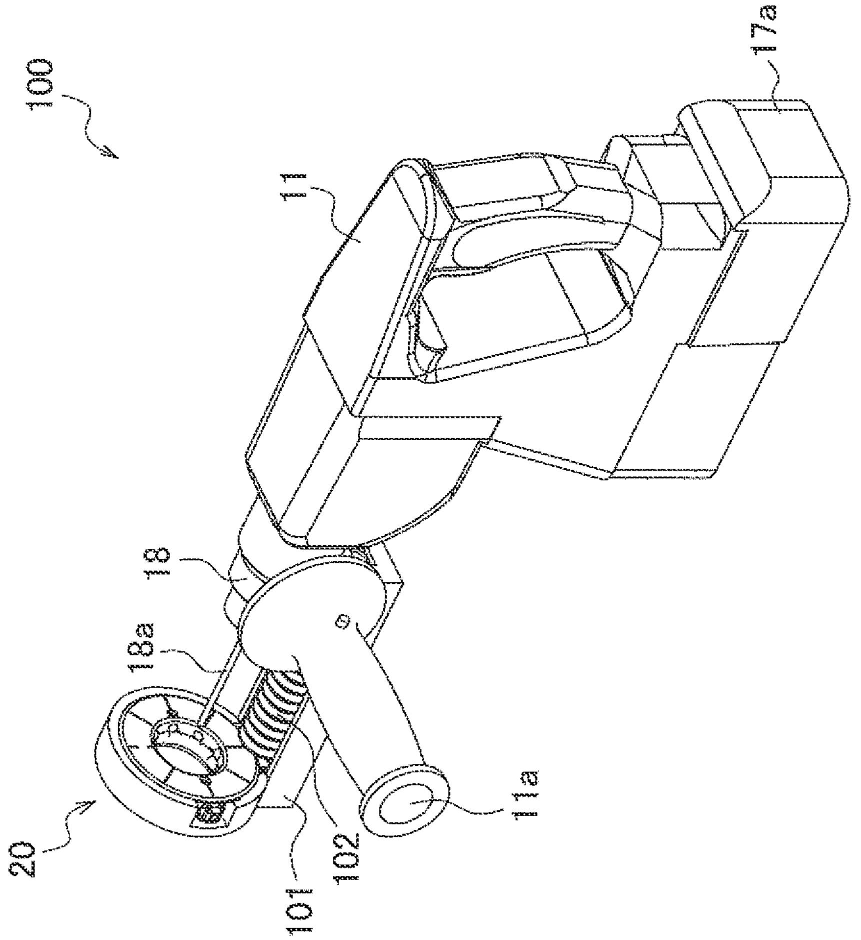
FIG. 20 is an oblique view of the configuration of a handheld power tool including the metal detector according to another embodiment of the present invention.

As shown in FIG. 20, the handheld power tool 100 of this embodiment does not have the dust collecting unit 40 of the first embodiment, and the metal detector 20 is attached to the distal end side via the holder 101.

Figure 21:
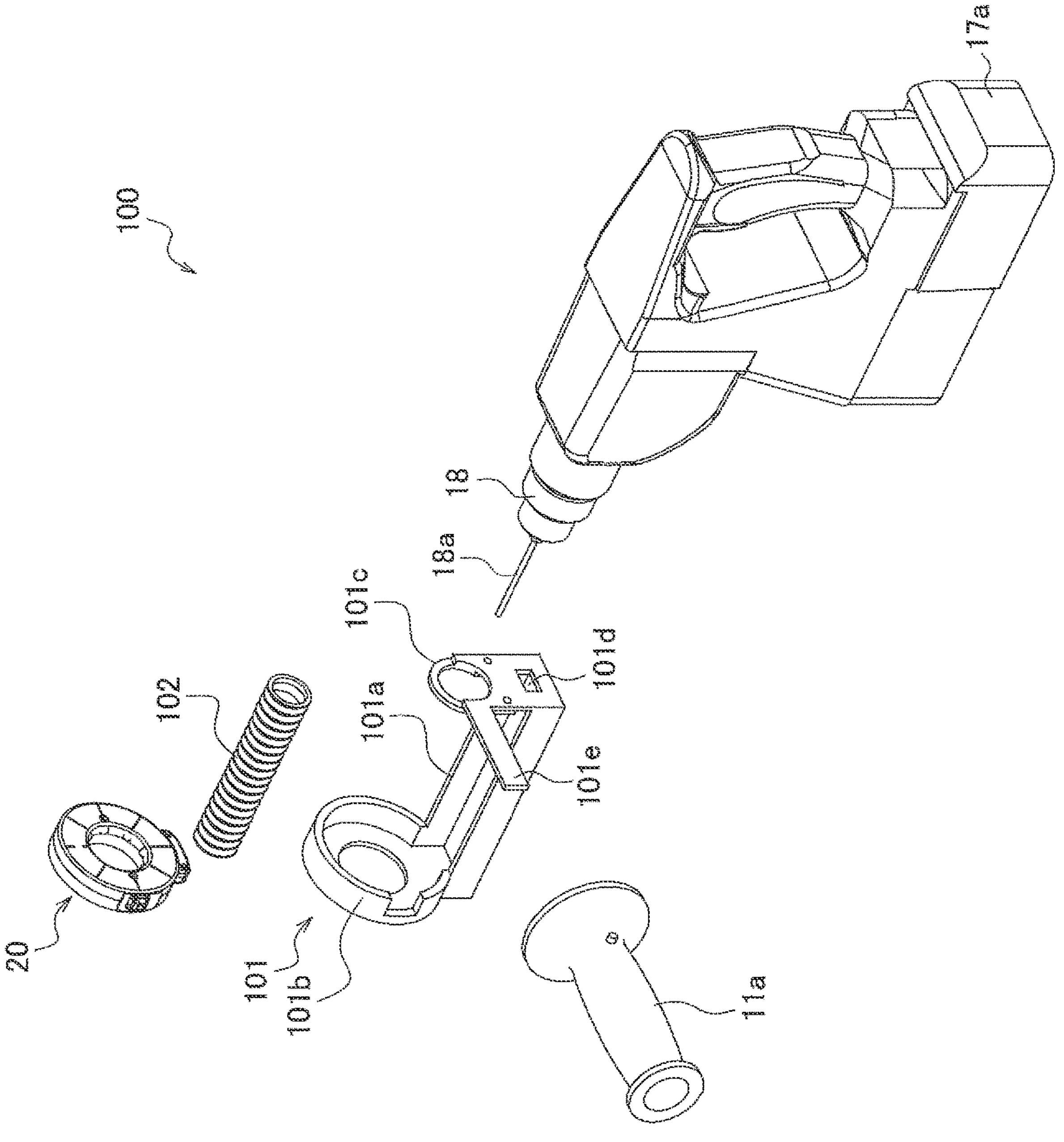
FIG. 21 is an exploded oblique view of the handheld power tool in FIG. 20.

As shown in FIG. 20, the holder 101 is attached to the distal end side of the main body 11 in order to integrate the main body 11 of the handheld power tool 100 with the metal detector 20. As shown in FIG. 21, the holder 101 has a telescoping beam 101*a*, a sensor holding portion 101*b*, a fixing portion 101*c*, a harness opening 101*d*, and a grip fixing portion 101*e*.

The telescoping beam 101*a* is a member that can be expanded and contracted toward the distal end side with respect to the main body 11, and a bellows member 102 through which a harness (not shown) is passed is disposed inside the concave shape.

This allows the length of the telescoping beam 101*a* to be adjusted to the proper length to match the length of the tip tool 18*a*, for example, and the telescoping beam 101*a* is extended when the tip tool 18*a* is to be attached to or detached from the tip portion 18, for example, which makes replacement much easier.

The sensor holding portion 101*b* is provided on the front end side of the holder 101, and the metal detector 20 is mounted from the rear end side.

The fixing portion 101*c* is a portion for fixing the holder 101 to the main body 11 of the handheld power tool 100, and the tip portion 18 of the main body 11 is inserted into the substantially annular portion thereof.

The harness opening 101*d* is an opening provided at the rear end of the holder 101, and a harness (not shown) is routed out of the metal detector 20 through the bellows member 102.

The grip fixing portion 101*e* is a member for fixing the grip portion 11*a*, and is provided so as to extend in a direction substantially perpendicular to the lengthwise direction of the holder 101.

The handheld power tool 100 in this embodiment is used in a state in which the metal detector 20 is integrated with the main body 11 via the holder 101.

This affords the same effect as that of the first embodiment.

Here, the handheld power tool 100 of this embodiment may be a handheld power tool 200 configured such that the metal detector 20 retracts from the position being worked by the tip tool 18*a* after the determination of the presence or absence of rebar W1 by the metal detector 20.

Figure 22A:
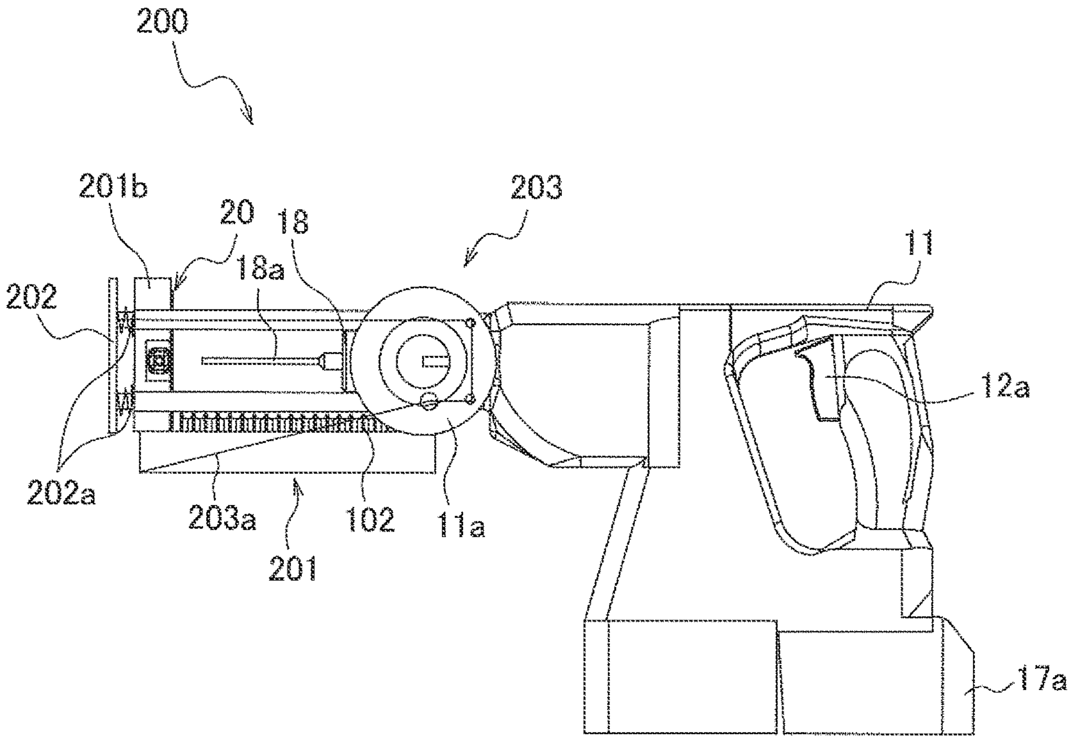
FIGS. 22A and 22B are side views illustrating a retracting mechanism included in the handheld power tool in FIG. 20.
Figure 22B:
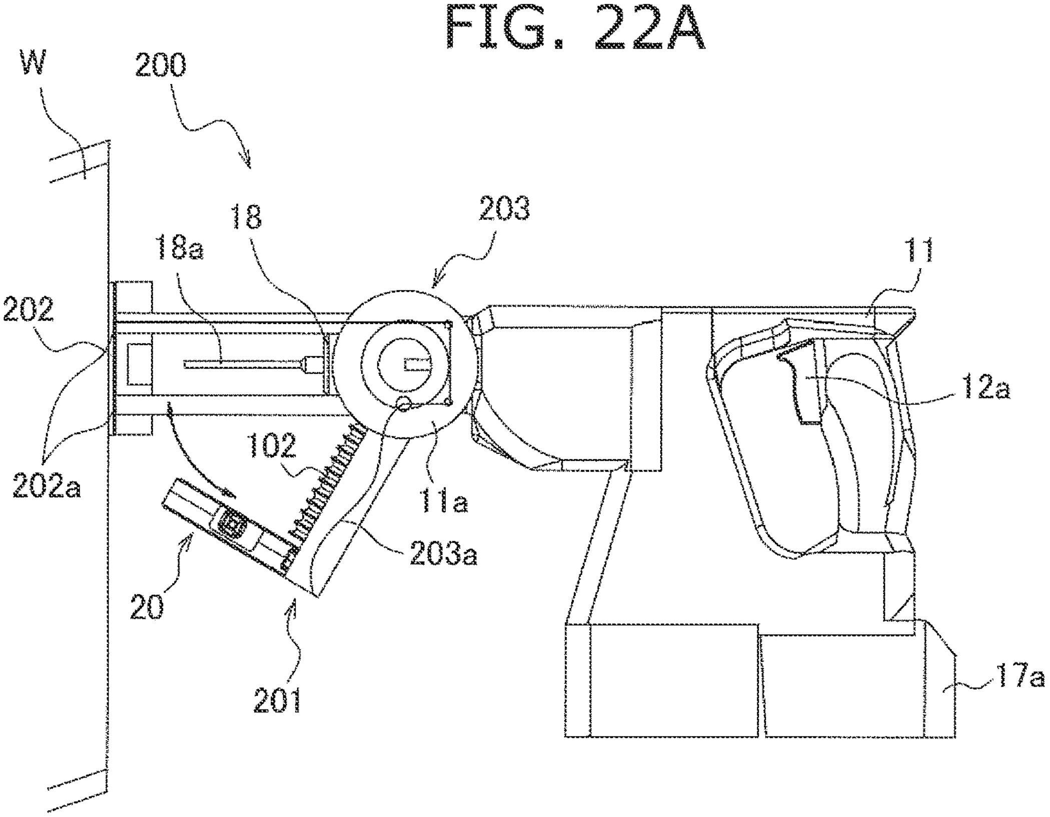

That is, as shown in FIGS. 22A and 22B, with the handheld power tool 200, when the metal detector 20 disposed at the distal end of the holder 101 is rotated (moved) downward, the metal detector 20 is retracted from near the tip tool 18*a* of the handheld power tool 200 so that drilling work can be performed.

A retracting mechanism 203 for retracting the metal detector 20 downward is provided near the connected portion between the main body 11 and a holder 201, and includes a wire 203*a* as shown in FIG. 22A.

The metal detector 20 is attached from the rear end side to a sensor holding portion 201*b* of the holder 201.

A contact detector (contact detection unit) 202 for detecting contact with the surface of the concrete W is provided on the distal end side of the sensor holding portion 201*b*.

The contact detector 202 is, for example, a strain sensor or a photosensor, is attached to the surface of the sensor holding portion 201*b* on the distal end side via the spring 202*a*, and upon coming into contact with the surface of the concrete W, a spring 202*a* contracts, resulting in a change from an OFF state to an ON state.

Figure 23:
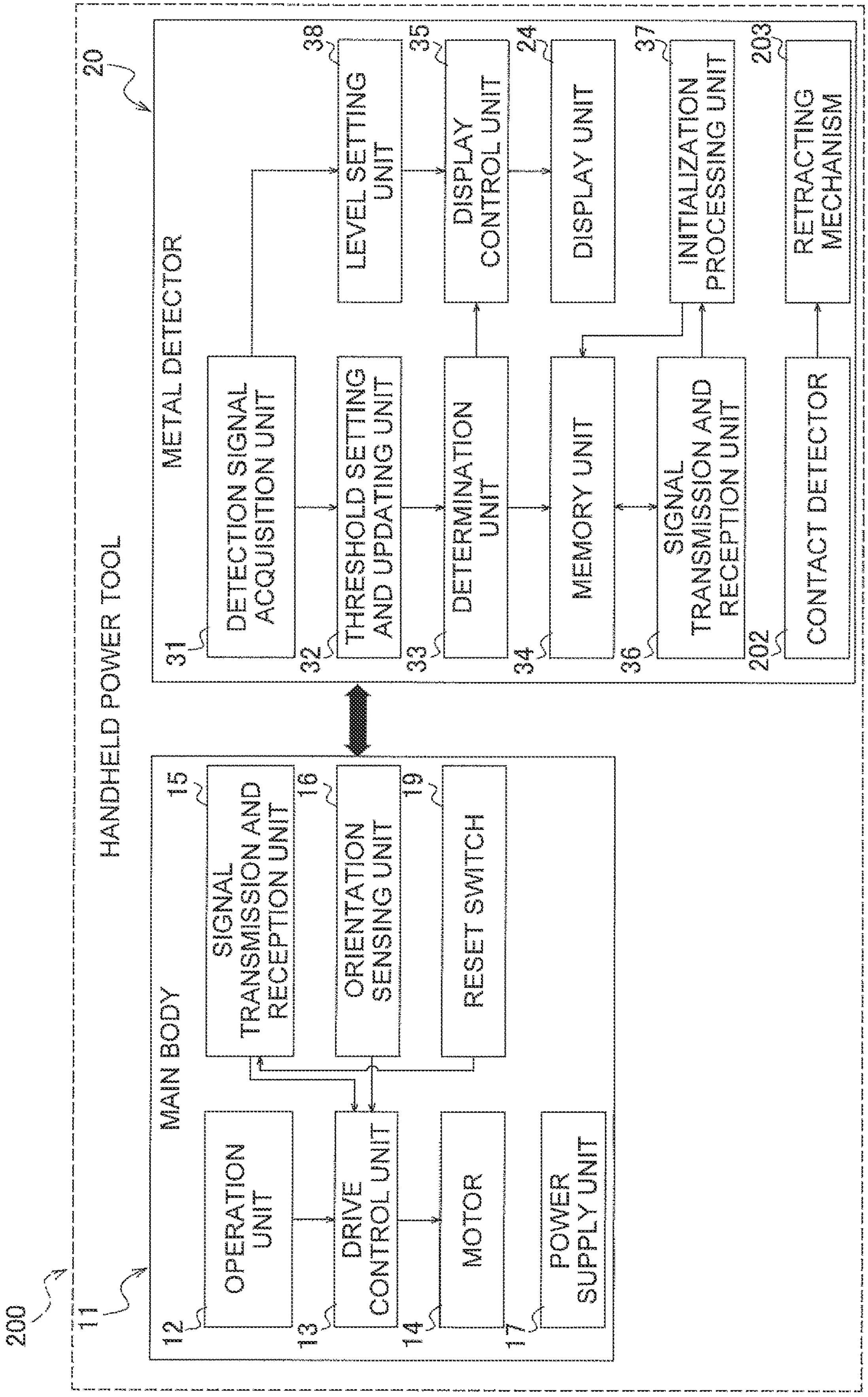
FIG. 23 is a control block diagram of the handheld power tool in FIG. 20.

Also, as shown in FIG. 23, the contact detector 202 is provided as a component of the metal detector 20. When contact with the concrete W surface is detected, the retracting mechanism 203 moves the metal detector 20 to the retraction position.

Consequently, the wire 203*a* of the retracting mechanism 203 goes from a taut state (see FIG. 22A) to a slack state (see FIG. 22B), the holder 201 is disengaged and rotates downward, and as a result, the metal detector 20 moves to a position where it is retracted from the vicinity of the tip tool 18*a*.

As a result, when the tip tool 18*a* is used to perform work on the concrete W, it is possible to reduce the load to which the metal detector 20 is subjected, such as exposure to dust and the application of vibration.

In this embodiment, an example was given in which the retracting mechanism 203 was operated when the contact detector 202 came into contact with the surface of the concrete W, but a push button switch or the like may be manually operated to retract the metal detector 20 from the distal end side of the handheld power tool 10, for example.

Also, the initialization processing unit 37 may perform initialization processing when the contact detector 202 detects contact with the surface of the concrete W.

Other Embodiments

An embodiment of the present invention was described above, but the present invention is not limited to or by the above embodiment, and various modifications can be made without departing from the gist of the invention.

(A)

In the above embodiment, an example was given in which the present invention was realized as the metal detector 20 and as a metal detection method in which this metal detector 20 was used. However, the present invention is not limited to this.

For instance, the present invention may be realized as a metal detection program that causes a computer to execute the above-mentioned metal detection method in which this metal detector is used.

This metal detection program is stored in a memory (memory unit) installed in a handheld power tool, and a CPU reads the program stored in the memory and causes the hardware to execute the various steps. More specifically, the same effect as above can be obtained by having the CPU read the metal detection program and execute the above-mentioned detection signal acquisition step, threshold value setting step, and determination step.

The present invention may also be realized as a recording medium on which this metal detection program is stored.

(B)

In the above embodiment, an example was given in which a plurality of rotatable rollers 46*a* were provided on the contact surface 46 formed on the distal end side of the metal detector 20. However, the present invention is not limited to this.

That is, it is preferable for the contact surface with the concrete surface to be configured or to undergo treatment so as to reduce frictional resistance, in order to make the work easier when scanning the metal detector over the concrete surface to detect rebar.

Figure 24A:
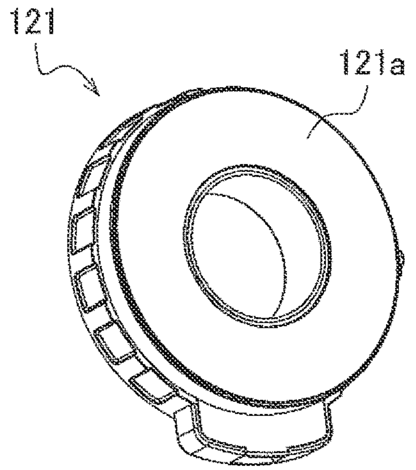
FIGS. 24A, 24B, and 24C are oblique views of the configuration of the metal detector according to another embodiment of the present invention.

For instance, as shown in FIG. 24A, a metal detector 121 may have a surface treated portion 121*a* (for reducing friction) formed on the side that comes into contact with the concrete.

Figure 24B:
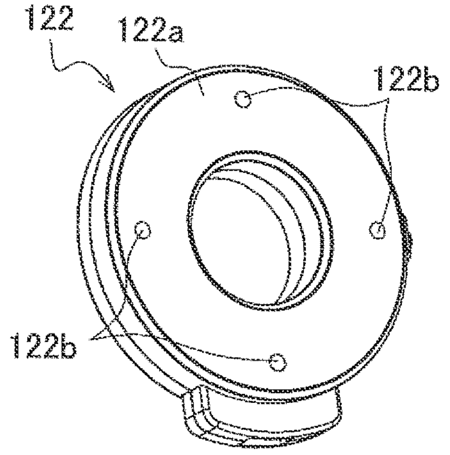

Also, as shown in FIG. 24B, a metal detector 122 may be provided with a plurality of balls 122*b* that rotate while in contact with the surface of the concrete, on a surface 122*a* that is on the side in contact with the concrete.

Figure 24C:
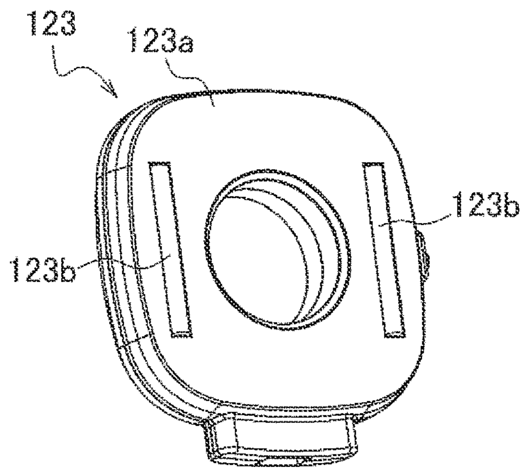

Furthermore, as shown in FIG. 24C, a metal detector 123 may be provided with two roller portions 123*b* that rotate while in contact with the surface of the concrete, on a surface 123*a* that is on the side in contact with the concrete.

With all of the above configurations, the metal detector can be moved smoothly over the concrete surface, which makes the work easier. Furthermore, the durability of the metal detector can be improved if the metal detector is not brought directly into contact with the concrete.

(C)

In the above embodiment, an example was given in which the threshold value setting and updating unit 32 set the maximum value of the detection signal as the upper limit threshold value and set the minimum value as the lower limit threshold value. However, the present invention is not limited to this.

For instance, in setting the threshold values, determination to detect metal may be performed by setting only the maximum value of the detection signal as the upper limit threshold value. Alternatively, determination to detect metal may be performed by setting only the minimum value of the detection signal as the lower limit threshold value.

(D)

In the above embodiment, an example was given in which the operator was notified of the detection result for the rebar W1 by the metal detector 20 by lighting lamps in the three colors of green, yellow, and red. However, the present invention is not limited to this.

For instance, the means for notifying of the detection result by the metal detector need not be expressing the result with light of different colors as in the above embodiment, and may instead be some other means, such as text information or voice information.

Also, in the above embodiment, an example was given in which the operator was notified of the approach (presence or absence) of metal by using three colors of light, but the operator may instead be notified of the approach of metal by using light of two colors or of four or more colors.

(E)

In the above embodiment, an example was given in which the operator was notified of the detection result for the rebar W1 by the metal detector 20 by lighting the eight LEDs 24*b* in a plurality of different colors. However, the present invention is not limited to this.

For instance, the display unit for turning on the lamps is not limited to eight LEDs, and seven or fewer, or nine or more LEDs may be used, or a light source other than LEDs may be used.

(F)

In the above embodiment, an example was given of a method for detecting rebar contained in concrete, in which an inductive type of metal detector was used that sensed the impedance of a detection coil, which changes with the eddy current generated in the metal as the metal (the object to be detected) approaches the magnetic field generated by passing a current through the coil included in the detector unit. However, the present invention is not limited to this.

For instance, a metal detector that employs some other method may be used, such as a capacitance type that senses changes in capacitance produced between the detector and the metal to be detected, or a high-frequency oscillation method that detects non-ferrous metal such as aluminum.

(G)

In the above embodiment, an example was given in which impedance changes in the winding coil 22*b* wound around the detector unit 22 were detected to detect the presence or absence of the rebar W1. However, the present invention is not limited to this.

For instance, a pattern type coil may be used instead of a wound coil to detect the changes in impedance and detect the metal.

(H)

In the above embodiment, an example was given in which the initialization processing of the detection result by the metal detector 20 either involved control performed depending on sensing the orientation of the handheld power tool 10, or was performed by pressing the reset switch 19. However, the present invention is not limited to this.

For instance, the initialization processing of the detection result by the metal detector may be configured so that only one of the above two controls can be performed, or initialization processing may be performed by some means other than the above two controls, such as a level gauge.

Also, the position of the reset switch used to perform initialization processing is not limited to the position described in the above embodiment, and this reset switch may instead be provided at some other position in the handheld power tool or the metal detector.

(I)

In the above embodiment, an example was given in which the metal detector 20 was used in a state where it could be attached to and detached from the main body 11 of the handheld power tool 10. However, the present invention is not limited to this.

For instance, the metal detector may be configured to be integrated with the main body of the handheld power tool in a non-detachable state.

Also, the metal detector may be used alone, separately from a handheld power tool.

(J)

In the above embodiment, an example was given in which concrete in which rebar was embedded served as the target to be subjected to work with the handheld power tool 10. However, the present invention is not limited to this.

For instance, the target may be drywall or another such wall material, and the handheld power tool may be one that performs any of various types of work while metal contained in the wall material is being detected.

Also, the metal in the target is not limited to being rebar, and may instead be some other metal member, such as a frame or a bolt.

(K)

In the above embodiment, an example was given in which the present invention was applied to a hammer drill as an example of the handheld power tool to which the metal detector 20 was attached. However, the present invention is not limited to this.

For instance, the handheld power tool to which the metal detector of the present invention is mounted may be some other handheld power tool, such as an impact drill or a vibration drill.

INDUSTRIAL APPLICABILITY

The metal detector of the present invention has the effect of allowing an operator to be notified of the presence or absence of metal inside a target such as concrete, without coming into contact with the metal, and therefore can be widely applied to various work tools that perform work while detecting metal.

The invention claimed is:

1. A metal detector that detects metal contained in a target, the metal detector comprising a memory and a processor configured with a program to perform operations comprising:

operation as a detection signal acquisition unit configured to acquire a detection signal which changes according to a detection intensity of the metal contained in the target, on a surface of the target;

operation as a threshold setting unit configured to set a threshold value used for determining a presence or absence of the metal on the basis of a maximum value and/or a minimum value included in an acquisition result for the detection signal acquired by the detection signal acquisition unit; and operation as a determination unit configured to determine the presence or absence of the metal by using the threshold value set in the threshold value setting unit.

2. The metal detector according to claim 1, wherein the processor configured with a program to perform operations such that operation as the threshold setting unit comprises setting the maximum value as an upper limit threshold value and sets the minimum value as a lower limit threshold value.

3. The metal detector according to claim 1, wherein the processor configured with a program to perform operations further comprising operation as an initialization processing unit configured to initialize the threshold value set in the threshold value setting unit.

4. The metal detector according to claim 1, wherein the processor configured with a program to perform operations further comprising operation as a memory unit configured to store the threshold values set by the threshold value setting unit in the memory.

5. The metal detector according to claim 4, wherein the processor configured with a program to perform operations further comprising operation as a threshold value updating unit configured to update the threshold value stored in the memory according to the acquisition result for the detection signal in the operation as the detection signal acquisition unit.

6. The metal detector according to claim 5, wherein the processor configured with a program to perform operations such that operation as the threshold value updating unit comprises repeatedly updating the threshold value during one scan of the target.

7. The metal detector according to claim 1, wherein the processor configured with a program to perform operations further comprising:

operation as a display unit configured to display a detection result of the metal; and operation as a display control unit configured to control the display unit.

8. The metal detector according to claim 7, wherein the processor configured with a program to perform operations such that operation as the display control unit comprises controlling the display unit so as to display light of different colors according to the detection intensity for the metal.

9. The metal detector according to claim 7, wherein the processor configured with a program to perform operations:

further comprising operation as a level setting unit configured to set a plurality of levels obtained by dividing up a level between a maximum value and a minimum value of the detection signal acquired by the detection signal acquisition unit at specific intervals, such that operation as the display control unit comprises performing control so as to switch a color of a light displayed on the display unit according to the plurality of levels set in the level setting unit.

10. The metal detector according to claim 1, wherein the processor configured with a program to perform operations further comprising operation as a contact detection unit configured to detect a contact with the target.

11. The metal detector according to claim 10, wherein the processor configured with a program to perform operations such that operation as the contact detection unit comprises operation as a contact switch configured to change from an OFF state to an ON state upon coming into contact with the target.

12. The metal detector according to claim 10, further comprising a retracting mechanism that is attached to the distal end of a handheld power tool which processes the target, and configured to retract from a distal end of the handheld power tool when operation as the contact detection unit detects contact with the target.

13. The metal detector according to claim 1, wherein the metal detector is removably attached to a handheld power tool configured to work the target.

14. A handheld power tool, comprising:

the metal detector according to claim 1;

a main body to which the metal detector is mounted;

a motor drive unit that is provided to the main body and configured to drive an attached distal end tool; and a motor drive control unit that is provided to the main body and configured to control the motor drive unit.

15. The handheld power tool according to claim 14, wherein the motor drive control unit prohibits a drive of the motor drive unit when operation as the determination unit has determined that metal is present.

16. The handheld power tool according to claim 14, wherein the motor drive control unit permits a drive of the motor drive unit when operation as the determination unit has determined that there is no metal.

17. A metal detection method that makes use of a metal detector that detects metal contained in a target, the metal detection method comprising:

a detection signal acquisition step in which a detection signal acquisition unit of the metal detector acquires a detection signal that changes according to a detection intensity for the metal contained in the target, on a surface of the target;

a threshold setting step in which a threshold value setting unit of the metal detector sets a threshold value that is used to determine a presence or absence of the metal, on the basis of a maximum value and/or a minimum value included in an acquisition results for the detection signal acquired in the detection signal acquisition step; and a determination step in which a determination unit of the metal detector determines the presence or absence of metal by using the threshold value set in the threshold value setting step.

18. A non-statutory computer readable medium storing a metal detection program for a metal detector that detects metal contained in a target, the metal detection program, when read and executed, causing a computer to execute a metal detection method comprising:

a detection signal acquisition step in which a detection signal acquisition unit of the metal detector acquires a detection signal that changes according to a detection intensity for the metal contained in the target, on a surface of the target;

a threshold setting step in which a threshold value setting unit of the metal detector sets a threshold value that is used to determine a presence or absence of the metal on the basis of a maximum value and/or a minimum value included in an acquisition results for the detection signal acquired in the detection signal acquisition step; and a determination step in which a determination unit of the metal detector determines the presence or absence of the metal by using the threshold value set in the threshold value setting step.

* * * * *